(12) United States Patent
Plemper et al.

(10) Patent No.: US 8,729,059 B2
(45) Date of Patent: May 20, 2014

(54) PARAMYXOVIRUS FAMILY INHIBITORS AND METHODS OF USE THEREOF

(75) Inventors: Richard K. Plemper, Decatur, GA (US); James P. Snyder, Atlanta, GA (US); Aiming Sun, Atlanta, GA (US)

(73) Assignee: Emory University, Atlanta, GA (US)

( * ) Notice: Subject to any disclaimer, the term of this patent is extended or adjusted under 35 U.S.C. 154(b) by 1057 days.

(21) Appl. No.: 12/526,373

(22) PCT Filed: Feb. 11, 2008

(86) PCT No.: PCT/US2008/053560
§ 371 (c)(1),
(2), (4) Date: Jul. 15, 2010

(87) PCT Pub. No.: WO2008/098239
PCT Pub. Date: Aug. 14, 2008

(65) Prior Publication Data
US 2011/0160188 A1 Jun. 30, 2011

Related U.S. Application Data

(60) Provisional application No. 60/900,658, filed on Feb. 9, 2007.

(51) Int. Cl.
*A01N 43/00* (2006.01)
*A61K 31/33* (2006.01)
(52) U.S. Cl.
USPC ........................................................ 514/183
(58) Field of Classification Search
None
See application file for complete search history.

(56) References Cited

U.S. PATENT DOCUMENTS

| | | |
|---|---|---|
| 6,399,354 B1 | 6/2002 | Knipe et al. |
| 2002/0119446 A1 | 8/2002 | Wertz et al. |

FOREIGN PATENT DOCUMENTS

| | | |
|---|---|---|
| EP | 08729509.3 | 3/2011 |
| EP | 11185817.1 | 1/2012 |
| WO | WO 2005013914 A2 * | 2/2005 |

OTHER PUBLICATIONS

Cremlyn, R. J.,et al., 1985, Chlorosulphonation of Thiophene and Furan-2-Carboxanilides, J Chem,Soc 8(3): 323-330.
Sun, A.,et al., 2007, Non-nucleoside inhibitors of the measles virus RNA-Depended RNA polymerase complex activity: Synthesis and in vitro evaluation, Bioorganic & Medicinal Chemistry Letters, 17, pp. 5199-5203.
Sun, A., et al., 2008, Potent Non-Nucleoside Inhibitors of the Measles Virus RNA-Depended RNA Polymerase Complex. J Med Chem, 51 pp. 3731-3741.
Duprex, et al, 1999, Observation of measles virus cell-to-cell spread in astrocytoma cells by using a green fluorescent protein-expressing recombinant virus, Journal of Virology, 73(11):9568-9575.
Marschall, et al. 2000, Recombinant green fluorescent protein-expressing human cytomegalvirus as a tool for screening antiviral agents, Antimicrobial Agents and Chemotherapy, 44(6)1588-1597.
Pelet, et al., 2005, High-throughput screening assay for negative single stranded RNA virus polymerase inhibitors, Journal of Virological Methods, 128:29-36.
Plemper, et al., 2004, A target site for template-based design of measles virus entry inhibitors, PNAS, 101 (15):5628-5633.
Plemper, et al., 2004, A target site for template-based design of measles virus entry inhibitors -Supporting Information-, PNAS, 101(15):5628-5633.
Towner, et al., 2005, Generation of eGFP expressing recombinant Zaire ebolavirus for analysis of early pathogenesis events and high-throughput antiviral drug screening, Virology, 332(1):20-27.
White, et al., 2007, Nonnucleoside inhibitors of measles virus RNA-dependent RNA polymerase complex activity, Antimicrobial Agents and Chemotherapy, 51(7):2293-2303.

* cited by examiner

*Primary Examiner* — Craig Ricci
*Assistant Examiner* — Jared D Barsky
(74) *Attorney, Agent, or Firm* — Emory Patent Group; James C. Mason; Susanne Hollinger

(57) ABSTRACT

Embodiments of the present disclosure include methods for identifying a compound or compounds useful as therapeutic agents in the treatment of paramyxovirus infections, compounds for the treatment of measles, and high throughput screening methods for identifying compounds capable of inhibiting the proliferation of a paramyxovirus.

10 Claims, 16 Drawing Sheets

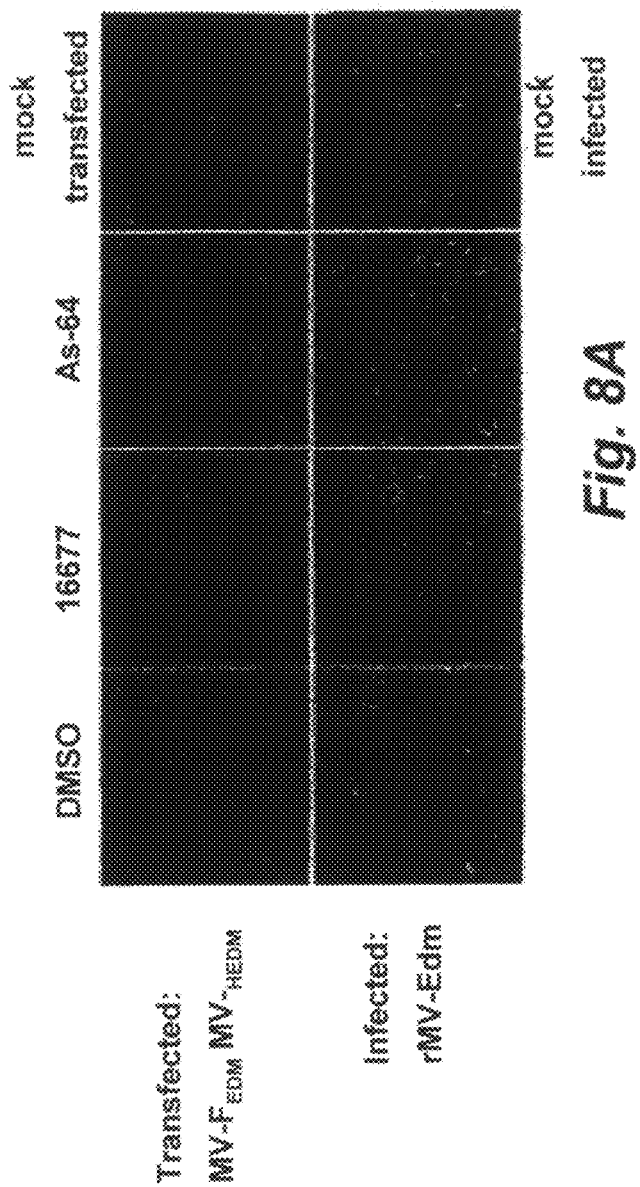

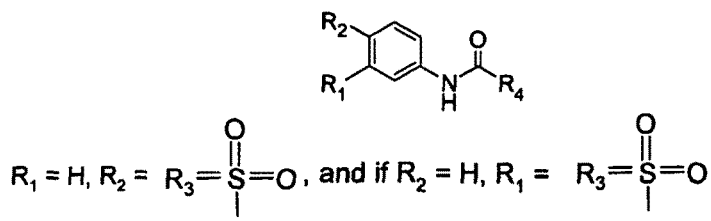

$R_1 = H, R_2 = R_3 - \overset{O}{\underset{O}{S}} = O$, and if $R_2 = H, R_1 = R_3 - \overset{O}{\underset{O}{S}} = O$

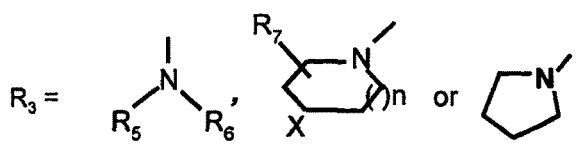

$R_5 = R_6$, $R_6$ = alkyl, aromatic or heterocyclic rings and substituents
$R_5 = H$, $R_6$ = alkyl, vinyl, acetylene, aromatic or a heterocyclic ring or substituents, and
$R_4$ is selected from the group:

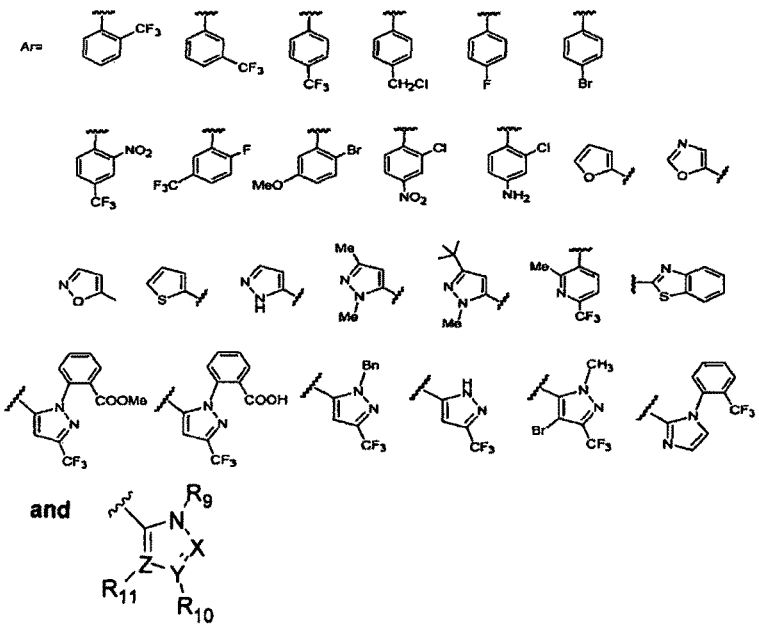

$R_9$: H, alkyl, $CH_2OH$, $CH_2NH_2$, $CH_2NHR$, $(CH_2)nX^1$ ($X^1$: OH, OR, $NH_2$, MHR)
$R_{10}$: $CH_3$, $CF_3$, Halo (Cl, Br, F), $CHF_2$, $CH_2F$, $CH_2OH$
$R_{11}$: H, alkyl, F, Cl, Br
X: N, CH, O, S
Y, Z: CH, N, O, S

*Fig. 11*

R$_8$ is alkyl, OH, NH$_2$, NO$_2$, CN or an aromatic group.

PARAMYXOVIRUS FAMILY INHIBITORS AND METHODS OF USE THEREOF

CROSS REFERENCE TO RELATED APPLICATION

This application claims priority to the PCT application entitled "Paramyxovirus Family Inhibitors and Methods of Use Thereof," having serial number PCT/US2008/53560, filed on Feb. 11, 2008. This application also claims priority to and benefit of U.S. Provisional Patent Application No. 60/900,658, filed on Feb. 9, 2007, which is incorporated by reference in its entirety.

STATEMENT ON FUNDING PROVIDED BY THE U.S. GOVERNMENT

This disclosure was made with government support under AI056179 and AI071002 awarded by the National Institutes of Health. The government has certain rights in the disclosure.

FIELD OF THE DISCLOSURE

The disclosure relates generally to methods for identifying a compound or compounds useful as therapeutic agents in the treatment of paramyxovirus infections. The compounds of the disclosure particularly relate to inhibitors of measles virus proliferation.

BACKGROUND

The paramyxovirus family of negative stranded enveloped RNA viruses contains highly contagious, clinically important pathogens such as measles virus (MV), respiratory syncytial virus, and human parainfluenza viruses (hPIV), and the recently emerged highly pathogenic Nipah and Hendra viruses (Wolfson et al., (2007) *Lancet* 369, 191-200; CDC. (2005) *MMWR* 54(8), 200-203)

MV remains a principal cause of worldwide morbidity and mortality, being responsible for approximately 300,000 to 400,000 deaths annually, despite the existence of a live-attenuated vaccine. Globally, measles is the leading cause of childhood death from a vaccine-preventable disease and remains among the ten most lethal human pathogens. Transmitted via the respiratory route, the virus is highly communicable and one of the most infectious pathogens identified (Griffin, D. E. (2001) *Measles Virus,* 4 Ed., Lippincott, Philadelphia, Pa.; Hethcote, H. W. (2000) *SIAM Review* 42(4), 599-653; van den Hof et al., (2002) *J. Infect Dis.* 186(10), 1483-1486). Prolonged immunosuppression following acute cases frequently predisposes patients to bacterial otitis media and bronchopneumonia. Complications include acute encephalitis in approximately 0.1% of cases, and subacute sclerosing panencephalitis (SSPE), a lethal late sequelae that occurs years after the primary infection (Griffin, D. E. (2001) *Measles Virus,* 4 Ed., Lippincott, Philadelphia, Pa.; Hilleman, M. R. (2001) *Vaccine* 20(5-6), 651-665).

Despite ongoing efforts to ultimately eradicate the virus (Moss & Griffin. (2006) *Nat. Rev. Microbiol.* 4(12), 900-908; Ota et al., (2005) *J. Neurovirol.* 11(5), 447-454), several factors contribute to the global persistence of MV and its resulting morbidity and mortality. It is estimated that a herd immunity of greater than 95% is required for complete suppression of the virus (Hethcote, H. W. (2000) *SIAM Review* 42(4), 599-653; Moss & Griffin. (2006) *Nat. Rev. Microbiol.* 4(12), 900-908; Ota et al., (2005) *J. Neurovirol.* 11(5), 447-454),). Maintaining fully protective herd immunity requires repeated vaccination since administration of a single dose at 12 months of age is not sufficient to meet this goal (Meissner et al., (2004) *Pediatrics* 114(4), 1065-1069; Watson et al., (1998) *MMWR Recomm. Rep.* 47(RR-8), 1-57). This constitutes a particular challenge in the developing world. In the US, a second dose of the vaccine is recommended for all school age children Pediatrics, A. A. O. (1989) *Pediatrics* 84, 2220-1113). Although high coverage rates are more readily achievable in developed countries, herd immunity has dropped significantly below the 95% level in several countries due to parental concerns about vaccine safety, resulting in lowered vaccination compliance. In recent years, coverage in certain areas of Europe has declined to less than 80%, resulting in significant measles outbreaks with a corresponding increase in hospitalizations and measles-associated deaths (van den Hof et al., (2002) *J Infect Dis* 186(10), 1483-1486; Jansen et al., (2003) *Science* 301(5634), 804; McBrien et al., (2003) *Pediatr. Infect. Dis. J* 22(7), 580-584). Lastly, immunity against the attenuated vaccine strain is less durable than that acquired naturally (Putz et al., (2003) *Int J Parasitol* 33(5-6), 525-545). In a fully vaccinated population, natural boosting by circulating wild-type virus is absent and half-lives of protective antibodies have been estimated at 25 years or less (Mossong et al., (1999) *Am J Epidemiol* 150(11), 1238-1249; Mossong et al., (2000) *Vaccine* 19(4-5), 523-529). In this environment of waning immunity, re-introduction of circulating virus in the population may be facilitated by individuals with weak immunity who may be protected against disease but not against infection (de Swart et al (2000) *Lancet* 355 (9199), 201-202; Whittle et al., (1999) *Lancet* 353(9147), 98-102), thus creating a basis for spontaneous outbreaks.

The only technology presently available to prevent measles virus infection is vaccination. Immunity takes weeks to develop, and vaccination is contra-indicated in immune compromised individuals. The current vaccines cannot be administered to infants due to interfering of maternal antibodies. Therapeutics for case management of measles and the rapid control of measles outbreaks are not available. For Nipah virus, no therapeutic or prophylactic strategies are in place. Taken together, these factors make highly desirable the development of cost-effective therapeutics against MV that augment the existing vaccination program by helping to control local outbreaks and manage cases of severe measles. Small molecule entry inhibitors could be made readily available to confer immediate protection, and could be safely administered to immune compromised patients to control acute MV or Nipah virus infection. These molecules could also be beneficial in treatment of complications of measles virus infection, such as the lethal sequelae subacute sclerosing panencephalitis.

MV infection is initiated by pH-independent fusion of the viral envelope with the target cell plasma membrane (Griffin, D. E. (2001) *Measles Virus,* 4 Ed., Lippincott, Philadelphia, Pa.). The hemagglutinin (H) envelope glycoprotein mediates particle attachment (Dorig et al., (1993) *Cell* 75(2), 295-305; Erlenhoefer et., (2001) *J Virol* 75(10), 4499-4505; Naniche et al., (1993) *J Virol* 67(10), 6025-6032; Tatsuo et al., (2000) *Nature* 406(6798), 893-897), followed by membrane fusion orchestrated by the fusion (F) envelope protein (Lamb et al., (2006) *Virology* 344(1), 30-37). Viral gene expression and subsequent genome replication then take place in the cytosol (Griffin, D. E. (2001) *Measles Virus,* 4 Ed., Lippincott, Philadelphia, Pa.). Both processes are mediated by the viral RNA-dependent RNA polymerase (RdRp) complex, which consists minimally of a homotetramer of the viral phosphoprotein (P) and a single polymerase (L) protein (Bourhis et al., (2006)

Virology 344(1), 94-110; Lamb & Kolakofsky, D. (2001) Paramyxoviridae: The viruses and their replication. In: Knipe, D. M.& Howley, P. M. (eds). *Fields Virology*, 4 Ed., Lippincott Williams & Wilkins, Philadelphia). Sole target for RdRp is a ribonucleoprotein complex of viral RNA encapsidated by the MV nucleocapsid (N) protein (Bourhis et al., (2006) *Virology* 344(1), 94-110), minimizing the presence of naked genomic RNA in the host cell. Considering that human and animal tissues lack a known homologue of the RdRp or the fusogenic envelope proteins, the polymerase complex and components of the entry machinery constitute particularly attractive targets for virus-specific small molecule inhibitors.

Despite its critical role in the viral life cycle, our mechanistic understanding of the MV RdRp is still limited and the structural characterization of its components is sparse. An abundance of structural disorder has been found in the MV N and P proteins, and no paramyxovirus polymerase has been purified thus far. In addition to their therapeutic potential, small molecule compounds targeting the MV RdRp complex may thus constitute viable tools for a better molecular and structural characterization of the viral replication machinery.

In contrast to the RdRp, considerable structural information is available for the paramyxovirus attachment and fusion protein, including structures of the latter in both the pre- and intermediate to post-fusion conformation. Relying on the molecular characterization of MV strains with distinct cytopathicity and a structural model of the MV F protein, we have in previous work identified a new class of MV fusion inhibitors, substituted anilides, in a structure-based drug design approach. The lead compound of this inhibitor class, AS-48 shows activity in the low micromolar range ($IC_{50}$=0.6 to 3.0 µM) against a panel of MV field isolates. A single Sub-Saharan isolate is resistant to inhibition by AS-48, however, and in vitro adaptation has resulted in the appearance of characteristic escape mutants after four to seven passages, suggesting that resistance may emerge rapidly in the field. The identification of additional drug candidates against MV with diverse target characteristics is therefore imperative. In addition to counteracting pre-existing resistance, combined administration of compounds with different target sites may reduce the rate of viral escape or result in impaired fitness of virions which develop multiple resistance.

SUMMARY

The disclosure relates generally to methods for identifying a compound or compounds useful as therapeutic agents in the treatment of paramyxovirus infections. The present disclosure encompasses robust, cell-based assays for high-throughput screening (HTS) of paramyxovirus, in particular of measles virus (MV) inhibitor candidates. Implementation of this assay has yielded several hit candidate compounds, which were subsequently confirmed in manual secondary assays. The structure of the most potent candidate was confirmed by independent synthesis. It has desirable drug-like properties, does not interfere with viral entry, and is not subject to cross-resistance with the AS-48 class of MV fusion inhibitors. Mechanistic characterization has revealed that the compound acts late in the viral life cycle.

The compounds of the disclosure are particularly advantageous in the treatment of measles. The disclosure, therefore, encompasses methods, including high throughput screening methods for identifying compounds capable of inhibiting the proliferation of a paramyxovirus, the methods comprising: infecting mammalian cells with a recombinant paramyxovirus capable of expressing a viral polypeptide; contacting a first culture of the infected mammalian cells with a test compound; determining the amount of expression of the viral polypeptide by the first cell culture; determining the amount of expression of the viral polypeptide by a second cell culture not in contact with the test compound, whereby a reduction in the viral polypeptide expression in the first cell culture relative to that in the second cell culture indicates that the test compound is capable of inhibiting the expression of a paramyxovirus gene.

In embodiments of the methods of the disclosure, the inhibition of the expression of the paramyxovirus gene may correlate with the ability of the test compound to inhibit proliferation of a paramyxovirus, and in particular of the measles virus, although it is considered within the scope of the disclosure for the methods to be applicable to identifying compounds capable of inhibiting other paramyxoviruses.

In the methods of the disclosure, the inhibition of the proliferation of the paramyxovirus gene is generally not by inhibiting the entry of the virus into a host cell or assembly of intact viral components in the cell, but to inhibiting the expression of the viral genes after entry and before assembly into intact virions.

In embodiments of the methods of the disclosure the expressed viral polypeptide can be operably linked to an indicator polypeptide, wherein the indicator polypeptide may be, but is not limited to, an enhanced fluorescence protein operably linked to a paramyxovirus-specific polypeptide. In one embodiment of the disclosure, the indicator polypeptide is an enhanced green fluorescence protein, and the amount of viral polypeptide expression is determined by measuring an amount of fluorescence.

Other embodiments of the methods of the disclosure provide high throughput screening methods suitable for the screening of chemical libraries of structurally related or unrelated compounds. The methods of the disclosure, therefore, may further comprise: obtaining a plurality of first mammalian cell cultures infected with a recombinant paramyxovirus; and contacting each first cell culture with at least one test compound of a plurality of compounds.

The high throughput methods of the disclosure for identifying a compound capable of inhibiting the proliferation of a paramyxovirus, comprises: obtaining a plurality of first mammalian cell cultures infected with a recombinant paramyxovirus, wherein the recombinant paramyxovirus is capable of expressing a viral polypeptide operably linked to an enhanced fluorescence protein; contacting each first cell culture with at least one test compound of a plurality of compounds; determining the amount of expression of the viral polypeptide by the first cell cultures; and determining the amount of expression of the viral polypeptide by a second cell culture not in contact with the test compound, whereby a reduction in the viral polypeptide expression in the first cell cultures relative to that in the second cell culture indicates that a test compound is capable of inhibiting the expression of a paramyxovirus gene, wherein the inhibition of the expression of the paramyxovirus gene correlates with the ability of the test compound to inhibit proliferation of a paramyxovirus, and wherein the inhibition of the proliferation of the paramyxovirus gene is not by inhibiting the entry of the virus into a host cell or assembly of intact viral components in the cell.

Another aspect of the disclosure is a compound (e.g. compounds such as, but not limited to, those compounds shown in FIGS. 2B, 2C and 11-13C) capable of inhibiting the proliferation of a paramyxovirus, wherein the compound comprises a sulfonamide group.

Embodiments of this aspect of the disclosure include, but are not limited to, structures such as 1-methyl-3-(trifluoromethyl)-N-[4-(pyrrolidinylsulfonyl)-phenyl]-1H-pyrazole-5- carboxamide (designated compound 16677), 1-methyl-N-(4-(piperidin-1-ylsulfonyl)phenyl)-3-(trifluoromethyl)-1H-pyrazole-5-carboxamide (designated AS-136A) and the like.

Yet another aspect of the disclosure are methods of inhibiting the proliferation of a paramyxovirus in a mammalian cell, comprising administering to the cell an effective amount of at least one paramyxovirus inhibitor composition, wherein the paramyxovirus inhibitor is a compound having the structures such as, but not limited to, 1-methyl-3-(trifluoromethyl)-N-[4-(pyrrolidinylsulfonyl)-phenyl]-1H-pyrazole-5-carboxamide (designated compound 16677), 1-methyl-N-(4-(piperidin-1-ylsulfonyl)phenyl)-3-(trifluoromethyl)-1H-pyrazole-5-carboxamide (designated AS-136A) and the like.

One embodiment of the disclosure comprises administering the effective dose to a recipient animal or human for the treatment of a paramyxovirus infection such as, but not only, a measles infection.

In one embodiment of this aspect of the disclosure, the administered composition comprises the compound 1-methyl-3-(trifluoromethyl)-N-[4-(pyrrolidinylsulfonyl)-phenyl]-1H-pyrazole-5-carboxamide (designated compound 16677).

BRIEF DESCRIPTION OF THE DRAWINGS

FIG. 8A illustrates that compound 16677 does not interfere with viral entry and is active late in the replicative cycle in that cell-to-cell fusion induced by transiently expressed MV glycoproteins is not inhibited by the compound. Transfected cells, treated with 15 µM compound 16677 or DMSO, were photographed after a 24-hour incubation period. For comparison, cells treated with the fusion inhibitor AS-48, cells infected with MV, and mock transfected/infected cells are also shown.

FIG. 11 illustrates the structures of embodiments of compounds of the disclosure.

DETAILED DESCRIPTION OF THE DISCLOSURE

Figure 1:
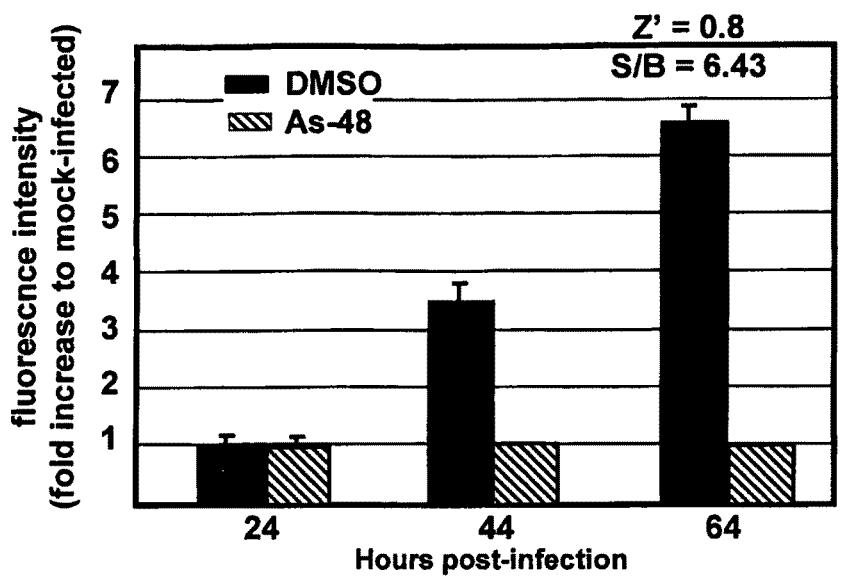
FIG. 1 illustrates the development of a robust cell-based assay for the automated identification of MV inhibitors. Cells seeded in microtiter plates in quadruplicates were infected at an MOI of 0.25 with rMV-eGFP and fluorescence intensity determined at the indicated times post-infection. For control, cells were infected with rMV-eGFP in the presence of 37.5 µM AS-48, an MV fusion inhibitor. Values indicate the fold-increase in fluorescence intensity as compared to mock-infected control cells. ($z'=1-(3\ SD_{(C)}+3\ SD_{(B)})/(Mean_{(C)}-Mean_{(B)})$ with C: control and B: background; S/B: signal to background ratio)

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein cited references"), as well as each document or reference cited in each of the herein-cited references (including any manufacturer's specifications, instructions, etc.), is hereby expressly incorporated herein by reference.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Embodiments of the present disclosure will employ, unless otherwise indicated, techniques of synthetic organic chemistry, biochemistry, biology, molecular biology, and the like, which are within the skill of the art. Such techniques are explained fully in the literature.

The methods of this disclosure are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It must be noted that, as used in the specification and the appended claims, the singular forms "a," "an," and "the" include plural referents unless the context clearly dictates otherwise. Thus, for example, reference to "a support" includes a plurality of supports.

In this specification and in the claims that follow, reference will be made to a number of terms that shall be defined to have the following meanings unless a contrary intention is apparent. As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

DEFINITIONS

In describing and claiming the disclosed subject matter, the following terminology will be used in accordance with the definitions set forth below.

In accordance with the present disclosure there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984), each of which is incorporated herein by reference.

Paramyxoviruses are viruses of the Paramyxoviridae family of the Mononegavirales order; they are negative-sense single-stranded RNA viruses responsible for a number of human and animal diseases, including, but not only, Newcastle disease virus) Hendravirus; Nipahvirus), Measles virus; Rinderpest virus, Canine distemper virus, phocine distemper virus) Sendai virus; Human parainfluenza viruses 1 and 3, as well some of the viruses of the common cold), Mumps virus; Simian parainfluenza virus 5, Menangle virus, and Tioman virus.

Virions are enveloped and can be spherical, filamentous or pleomorphic. Fusion proteins and attachment proteins appear as spikes on the virion surface. Matrix proteins inside the envelope stabilise virus structure. The nucleocapsid core is composed of the genomic RNA, nucleocapsid proteins, phosphoproteins and polymerase proteins. The genome consists of a single segment of negative-sense RNA, 15-19 kilobases in length and containing 6-10 genes. Extracistronic (non-coding) regions include a 3' leader sequence, 50 nucleotides in length which acts as a transcriptional promoter, a 5' trailer sequence, 50-161 nucleotides long, intergenomic regions between each gene which are three nucleotides long for morbillivirus, respirovirus and henipavirus, variable length (1-56 nucleotides) for rubulavirus and pneumovirinae. Each gene contains transcription start/stop signals at the beginning and end which are transcribed as part of the gene. Gene sequence within the genome is nucleocapsid-phosphoprotein-matrix-fusion-attachment-large (polymerase)

The virion proteins include: N—the nucleocapsid protein associates with genomic RNA (one molecule per hexamer) and protects the RNA from nuclease digestion; P—the phosphoprotein binds to the N and L proteins and forms part of the RNA polymerase complex; M—the matrix protein assembles between the envelope and the nucleocapsid core, it organises and maintains virion structure; F—the fusion protein projects from the envelope surface as a trimer, and mediates cell entry by inducing fusion between the viral envelope and the cell membrane by class I fusion. H/HN/G—the cell attachment proteins span the viral envelope and project from the surface as spikes. They bind to sialic acid on the cell surface and facilitate cell entry. Proteins are designated H for morbilliviruses and henipaviruses as they possess haemagglutination activity, observed as an ability to cause red blood cells to clump. HN attachment proteins occur in respiroviruses and rubulaviruses. These possess both haemagglutination and neuraminidase activity which cleaves sialic acid on the cell surface, preventing viral particles from reattaching to previously infected cells. Attachment proteins with neither haemagglutination nor neuraminidase activity are designated G (glycoprotein). These occur in members of pneumovirinae; L—the large protein is the catalytic subunit of RNA dependent RNA polymerase (RDRP); accessory proteins—a mechanism known as RNA editing (see Mononegavirales) allows multiple proteins to be produced from the P gene. These are not essential for replication but may aid in survival in vitro or may be involved in regulating the switch from mRNA synthesis to anti-genome synthesis.

The term "inhibition of proliferation" as used herein refers to inhibiting the assembly of intact and infectious paramyxovirus virions.

The term "organism" or "host" refers to any living entity comprised of at least one cell. A living organism can be as simple as, for example, a single eukaryotic cell or as complex as a mammal, including a human being. As used herein, the term "host" includes humans, mammals (e.g., cats, dogs, horses, chicken, pigs, hogs, cows, and other cattle), and other living species that are in need of treatment. In particular, the term "host" includes humans. Hosts that are "predisposed to" condition(s) can be defined as hosts that do not exhibit overt symptoms of one or more of these conditions but that are genetically, physiologically, or otherwise at risk of developing one or more of these conditions. The term "host" as used herein further refers to an isolated cell from a mammal or human including a cultured cell or cell line.

The term "treat", "treating", and "treatment" are an approach for obtaining beneficial or desired clinical results. Specifically, beneficial or desired clinical results include, but are not limited to, alleviation of symptoms, diminishment of extent of disease, stabilization (e.g., not worsening) of disease, preventing spread of disease, preventing the disease from occurring in an animal that may be predisposed to the disease but does not yet experience or exhibit symptoms of the disease (prophylactic treatment), delaying or slowing of disease progression, amelioration or palliation of the disease state, and remission (partial or total) whether detectable or undetectable. In addition, "treat", "treating", and "treatment" can also mean prolonging survival as compared to expected survival if not receiving treatment.

The term "condition" and "conditions" denote a state of health that can be related to infection by a virus. The infections that are discussed herein are to be included as conditions that can be treated by embodiments of the present disclosure.

The term "nucleic acid" or "polynucleotide" is a term that generally refers to a string of at least two base-sugar-phosphate combinations. As used herein, the term includes deoxyribonucleic acid (DNA) and ribonucleic acid (RNA) and generally refers to any polyribonucleotide or polydeoxyribonucleotide, which may be unmodified RNA or DNA or modified RNA or DNA. RNA may be in the form of an tRNA (transfer RNA), snRNA (small nuclear RNA), rRNA (ribosomal RNA), mRNA (messenger RNA), anti-sense RNA, RNAi, siRNA, and ribozymes. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid sequence" or "oligonucleotide" also encompasses a nucleic acid or polynucleotide as defined above.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein.

The term also includes PNAs (peptide nucleic acids), phosphorothioates, and other variants of the phosphate backbone of native nucleic acids. Natural nucleic acids have a phosphate backbone; artificial nucleic acids may contain other types of backbones, but contain the same bases. Thus, DNAs or RNAs with backbones modified for stability or for other reasons are "nucleic acids" or "polynucleotides" as that term is intended herein.

"Polypeptide" refers to peptides, proteins, glycoproteins, and the like, of the present disclosure comprising two or more amino acids joined to each other by peptide bonds or modified peptide bonds, (e.g., peptide isosteres). "Polypeptide" refers to both short chains, commonly referred to as peptides, oligopeptides, or oligomers, and to longer chains, generally referred to as proteins.

Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Polypeptides" may contain amino acids other than the 20 gene-encoded amino acids. "Polypeptides" include amino acid sequences modified either by natural processes, such as post-translational processing, or by chemical modification techniques, which are well known in the art. Such modifications are described in basic texts and in more detailed monographs, as well as in a voluminous research literature.

Modifications may occur anywhere in the polypeptides of the present disclosure, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched, and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (Proteins-Structure and Molecular Properties, 2nd Ed., T. E. Creighton, W. H. Freeman and Company, New York, 1993; Wold, F., Post-translational Protein Modifications: Perspectives and Prospects, pgs. 1-12 in Post-translational Covalent Modification of Proteins, B. C. Johnson, Ed., Academic Press, New York, 1983; Seifter, et al., *Meth. Enzymol.,* 182: 626-646, (1990), and Rattan, et al., *Ann NY Acad. Sci.,* 663: 48-62, (1992)).

"Variant" refers to polypeptides of the present disclosure that differ from a reference polynucleotide or polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, and deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

An "expression construct" is an expression vector containing a coding sequence for a recombinant protein.

The term "recombinant" when used with reference to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant) form of the cell or express native genes that are otherwise abnormally expressed, under-expressed or not expressed at all. The term "recombinant" generally refers to a non-naturally occurring nucleic acid. Such non-naturally occurring nucleic acids include combinations of DNA molecules of different origin that are joined using molecular biology technologies, or natural nucleic acids that have been modified, for example that have deletions, substitutions, inversions, insertions, etc. Recombinant also refers to the polypeptide encoded by the recombinant nucleic acid. Non-naturally occurring nucleic acids or polypeptides include nucleic acids and polypeptides modified by man.

The term "heterologous" indicates derived from a separate genetic source, a separate organism, or a separate species. Thus, a heterologous antigen is an antigen from a first genetic source expressed by a second genetic source. The second genetic source is typically a vector.

The term "operably linked" refers to the arrangement of various nucleotide sequences relative to each other such that the elements are functionally connected to and are able to interact with each other. Such elements may include, without limitation, one or more promoters, enhancers, polyadenylation sequences, and transgenes. The nucleotide sequence elements, when properly oriented, or operably linked, act together to modulate the activity of one another, and ultimately may affect the level of expression of the transgene. For example, control sequences or promoters operably linked to a coding sequence are capable of effecting the expression of the coding sequence, and an organelle localization sequence operably linked to protein will direct the linked protein to be localized at the specific organelle. The position of each element relative to other elements may be expressed in terms of the 5' terminus and the 3' terminus of each element, and the distance between any particular elements may be referenced by the number of intervening nucleotides, or base pairs, between the elements.

A "vector" is a genetic unit (or replicon) to which or into which other DNA segments can be incorporated to effect replication, and optionally, expression of the attached segment. Examples include, but are not limited to, plasmids, cosmids, viruses, chromosomes and minichromosomes. Exemplary expression vectors include, but are not limited to, baculovirus vectors, modified vaccinia Ankara (MVA) vectors, plasmid DNA vectors, recombinant poxvirus vectors, bacterial vectors, recombinant baculovirus expression systems (BEVS), recombinant rhabdovirus vectors, recombinant alphavirus vectors, recombinant adenovirus expression systems, recombinant DNA expression vectors, and combinations thereof.

A "coding sequence" is a nucleotide sequence that is transcribed into mRNA and translated into a protein, in vivo or in vitro.

"Regulatory sequences" are nucleotide sequences, which control transcription and/or translation of the coding sequences that they flank.

"Pharmaceutically acceptable salts" include, but are not limited to, the acid addition salts of compounds of the present disclosure (formed with free amino groups of the peptide) which are formed with inorganic acids (e.g., hydrochloric acid or phosphoric acids) and organic acids (e.g., acetic, oxalic, tartaric, or maleic acid). Salts formed with the free carboxyl groups may also be derived from inorganic bases (e.g., sodium, potassium, ammonium, calcium, or ferric hydroxides), and organic bases (e.g., isopropylamine, trimethylamine, 2-ethylamino-ethanol, histidine, and procaine).

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The term "alkyl" refers to straight or branched chain unsubstituted hydrocarbon groups of 1 to 20 carbon atoms, preferably 1 to 12 carbon atoms. The expression "lower alkyl" refers to unsubstituted alkyl groups of 1 to 4 carbon atoms.

The terms "substituted alkyl", "substituted alkenyl" or "substituted alkynyl" refer to an alkyl, alkenyl or alkynyl group substituted by, for example, one to four substituents, such as halo, trifluoromethyl, trifluoromethoxy, hydroxy, alkoxy, cycloalkyloxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, (arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as indolyl, imidazolyl, furyl, thienyl, thiazolyl, pyrrolidinyl, pyridyl, pyrimidyl and the like. Where noted above where the substituent is further substituted it will be with halogen, alkyl, alkoxyaryl or aralkyl. Preferred substitutions are halo, $SO_3H$, and $CO_2H$.

The term "halogens or "halo" refers to fluorine, chlorine, bromine, and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" or "alkylaryl" refers to an aryl group bonded directly through an alkyl group, such as benzyl or phenethyl.

The term "substituted aryl" or "substituted alkylaryl" refers to an aryl group or alkylaryl group substituted by, for example, one to four substituents such as alkyl, substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl. "Substituted benzyl" refers to a benzyl group substituted by, for example, any of the groups listed above for substituted aryl.

The term "cycloalkyl" refers to optionally substituted, saturated cyclic hydrocarbon ring systems, preferably containing 1 to 3 rings and 3 to 7 carbons per ring which may be further fused with an unsaturated $C_3$-$C_7$ carbocyclic ring. Exemplary groups include cyclopropyl, cyclobutyl, cyclopentyl, cyclohexyl, cycloheptyl, cyclooctyl, cyclodecyl, cyclododecyl and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom and at least one carbon atom in the ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dixolane and tetrahydro-1,1-dioxothienyl, dioxanyl, isothiazolidinyl, thietanyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl, or furo[2,3-b]pyridinyl), dihydroisoindolyl, diyhydroquinazolinyl (such as 3,4-dihydro-4-oxo-quinazolinyl), benzisothiazolyl, benzisoxazolyl, benzodiazinyl, benzofurazanyl, benzothiopyranyl, benzothiazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents.

The term "heteroatoms" shall include oxygen, sulfur and nitrogen.

Within the above-described definitions, certain embodiments may be preferred. Preferred alkyl groups are lower alkyl groups containing 1 to 12 carbon, and more preferably 1 to about 5 carbon atoms, and can be straight, branched-chain or cyclic saturated aliphatic hydrocarbon groups.

Examples of suitable alkyl groups include methyl, ethyl and propyl. Examples of branched alkyl groups include isopropyl and t-butyl. An example of a suitable alkylaryl group is phenethyl. Examples of suitable cycloalkyl groups typically contain 3-8 carbon atoms and include cyclopropyl, cyclobutyl, cyclopentyl and cyclohexyl. The aromatic or aryl groups are preferably phenyl or alkyl substituted aromatic groups (aralkyl) such as phenyl $C_{1-3}$ alkyl such as benzyl.

The N-heterocyclic rings preferably contain 3-7 atoms in the ring and a heteroatom such as N, S or O in the ring. Examples of suitable preferred heterocyclic groups are pyrrolidino, azetidino, piperidino, 3,4-didehydropiperidino, 2-methylpiperidino and 2-ethylpiperidino. In addition, the above substitutions can include halo such as F, Cl, Br, lower alkyl, lower alkoxy and halo substituted lower alkoxy.

Pharmaceutically acceptable salts of the compounds of formula (I) include those identified from pharmaceutically acceptable, inorganic and organic acids and bases. Examples of suitable acids include hydrochloric, hydrobromic, sulphuric, nitric, perchloric, fumaric, maleic, phosphoric, glycolic, lactic, salicylic, succinic, toluene-p-sulphonic, tartaric, acetic, citric, methanesulphonic, formic, benzoic, malonic, naphthalene-2-sulphonic, trifluoroacetic and benzenesulphonic acids.

Salts derived from appropriate bases include alkali such as sodium and ammonia.

The terms "effective amount" and therapeutically-effective amount" as used herein means that amount of a compound, material, or composition comprising a compound or composition of the present disclosure, and which is effective for producing some desired therapeutic effect against a paramyxovirus infection, particularly, but not limited to, a measles infection.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or an encapsulating material such as liposomes, polyethylene glycol (PEG), PEGylated liposomes, nonoparticles and the like, involved in carrying or transporting the subject compositions or therapeutic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

It is of course understood that the compounds of the present disclosure relate to all optical isomers and stereo-isomers at the various possible atoms of the molecule.

Discussion

Figure 2A:
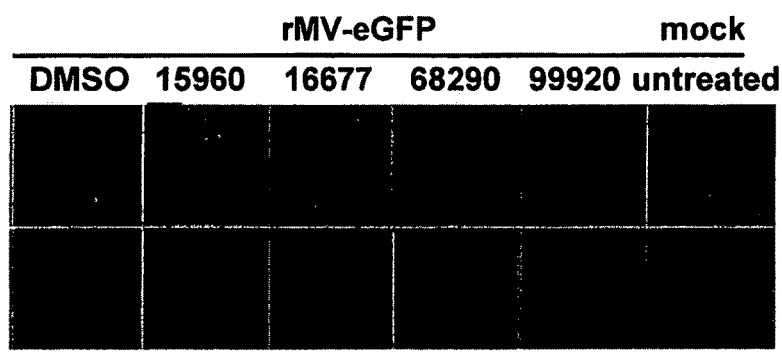
FIG. 2A illustrates phase-contrast and fluorescence microphotographs of cells infected with rMV-eGFP in the presence of 25 µM compound. Controls included cells infected with rMV-eGFP in the presence of equal volumes of DMSO and mock-infected cells. Representative fields of view are shown.
Figure 2B:
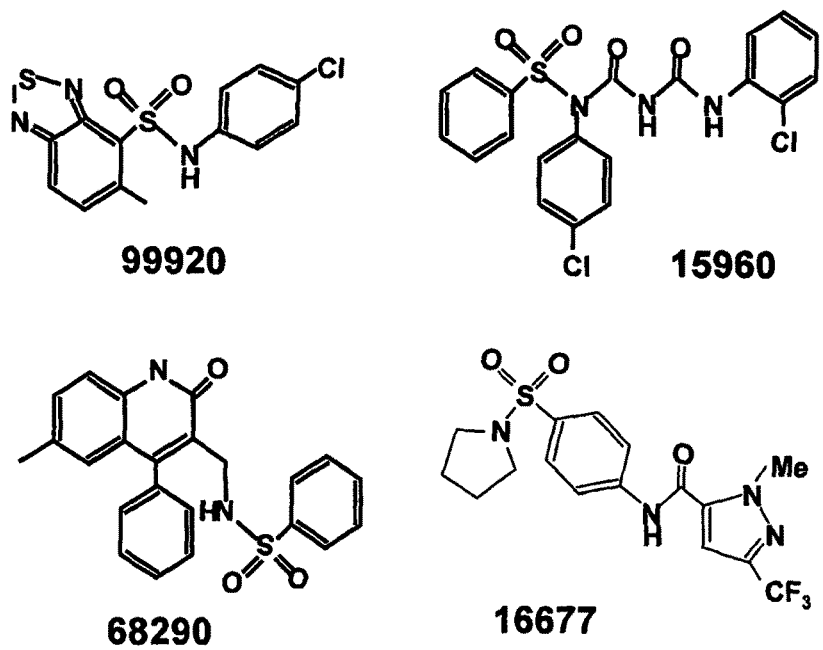
FIG. 2B illustrates the chemical structures of four illustrative hit candidates identified in FIG. 2A.

The disclosure relates generally to methods, including high throughput screening methods, for identifying a compound or compounds useful as therapeutic agents in the treatment of paramyxovirus infections. The present disclosure encompasses methods for the identification of potential small-molecule inhibitors of MV proliferation. The disclosed methods are based on a recombinant measles virus that expresses eGFP as an additional transcription unit, and under the transcriptional control of MV genetic elements. The initial screening methods may be complemented by one or more confirmatory assays that assess cytotoxicity, antiviral activity and chemical structure of those compounds identified by the screening procedure. The methods of this disclosure are advantageous for the screening of libraries of chemical compounds to select those compounds showing efficacy against the proliferation of MV in mammalian cells. The methods are also advantageous for the automated screening procedures to dramatically expanding the number of compounds that may be tested in a given period thereby offering significant cost benefits.

Suitability of the assay for hit identification was shown by using as positive control a small-molecule MV entry inhibitor, AS-48 (Plemper et al., (2005) *Antimicrob. Agents Chemother.* 49(9), 3755-3761; Sun et al., (2006) *J. Med. Chem.* 49(17), 5080-5092). In addition to a favorable z' value and signal-to-background ratio, assay evaluation revealed little wall effects or cross-fluorescence between wells, allowing cost-effective use of the full area of standard microtiter plates. A pilot screen of a 34,000 compound proprietary library of Emory University yielded at least four confirmed hits (the structures of which are shown in FIG. 2B)> All four of the compounds identified as inhibitors of the expression of MV genes harbor a sulfonamide group, although chemically they belong to different structural classes.

The identification of promising small-molecule inhibitors can be hampered by promiscuous compounds that frequently emerge in screens of compound libraries (McGovern et al., (2002) *J. Med. Chem.* 45(8), 1712-1722; McGovern et al., (2003) *J. Med. Chem.* 46(8), 1478-1483). Rather than docking to defined target areas, promiscuous compounds are thought to act non-specifically through adsorption or absorption of target structures to larger compound aggregates. Non-specific and non-competitive binding ultimately leads to flat structure-activity relationships, typically in the low micromolar range, that usually render chemical efforts to improve biological activity futile (McGovern et al., (2002) *J. Med. Chem.* 45(8), 1712-1722; McGovern et al., (2003) *J. Med. Chem.* 46(8), 1478-1483). The addition of a high amount of bovine serum albumin (BSA) and an increase in the amount of infectious particles did not affect the $IC_{50}$ concentration determined for the most potent, compound 16677, of the four compounds identified. Indicating that this compound was a well-behaved inhibitor of MV. This was further confirmed by its high target specificity.

Yields of hPIV2, a distantly related paramyxovirus, were unaffected by compound 16677. CDV, a closely related member of the same genus as MV, was only mildly inhibited. Selective inhibition of MV also corroborated the results of the cytotoxicity assays. General interference with host cellular functions, which would likely be unspecific, could be discounted as the underlying mechanism of antiviral activity of the compound 16677.

Figure 7:
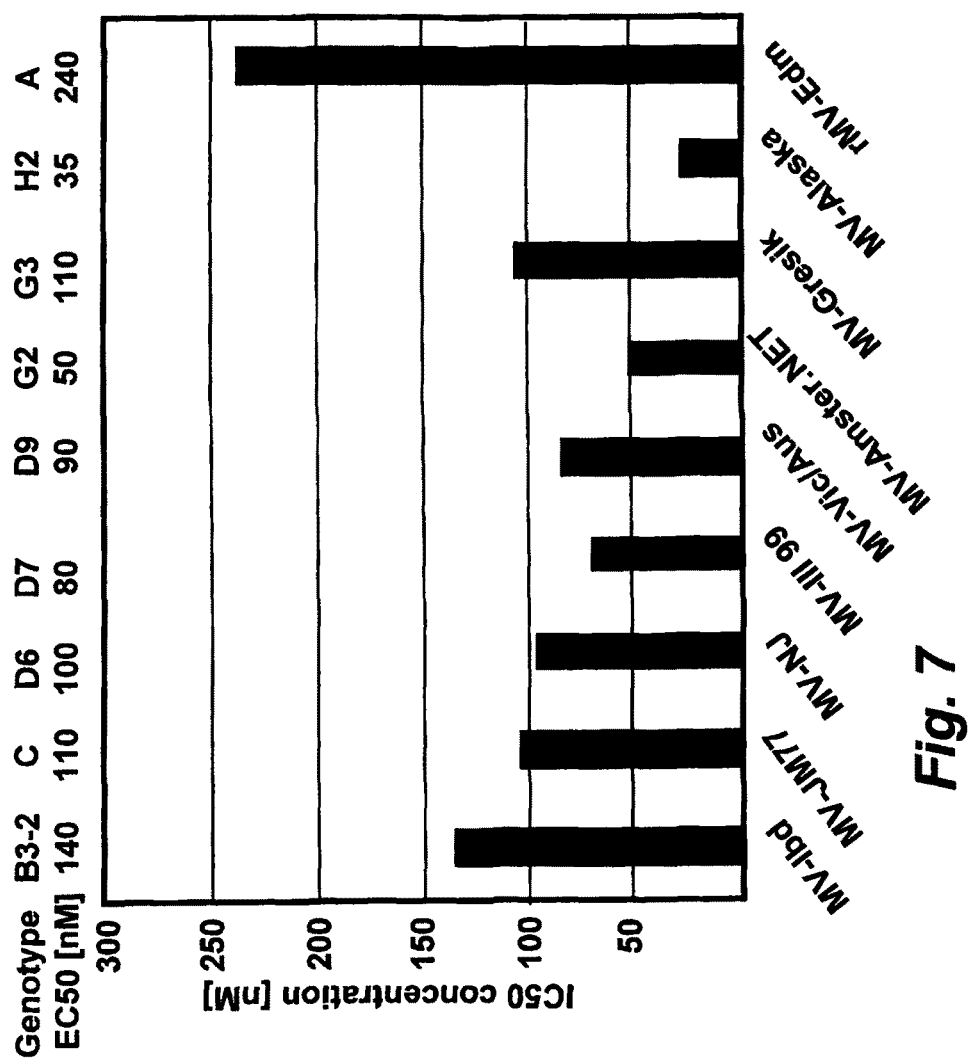
FIG. 7 illustrates that compound 16677 is active against a panel of clinical MV isolates. Dose-response curves were generated on the basis of virus yields determined by $TCID_{50}$ titration and $IC_{50}$ concentrations calculated. Average $IC_{50}$ concentrations based on three experiments and viral genotypes are given above the graph; standard deviations are shown.

Compound 16677 showed activity in the low nanomolar range against a panel of MV field isolates as shown in FIG. 7. These isolates used represented currently circulating genotypes, thus underscoring the therapeutic potential of the compound. Importantly, the panel of viruses examined includes the MV-Ibd isolate of genotype B3, which has been found to be naturally resistant to the AS-48 MV entry inhibitor class (Doyle et al., (2006) *J. Virol.* 80(3), 1524-1536). Lack of cross-resistance of compound 16677 with this inhibitor class indicates a different mechanism of antiviral activity for compound 16677 and opens potential avenues to counteract spontaneous viral resistance that may develop in the field.

Consistent with the absence of cross-resistance with the MV fusion inhibitors and in contrast to the findings obtained for compound AS-48, compound 16677 did not prevent cell-to-cell fusion mediated by plasmid-encoded H and F MV glycoproteins and showed no inhibitory activity in an MV entry assay. Time-of-addition assays showed that compound 16677 potently inhibits MV even when added late in the replicative cycle.

These observed results with compound 16677 indicate that it likely mode of action is interference with the viral RNA-dependent RNA polymerase complex. The screening methods encompassed by the present disclosure do not favor the identification of viral assembly inhibitors. Such inhibitors would act downstream of viral gene expression and hence would not interfere with eGFP expression from the recombinant paramyxovirus of the disclosed methods.

A minigenome reporter assay that monitors the activity of the viral RNA polymerase complex confirmed this hypothesis, since it demonstrated dose-dependent inhibition of MV minigenome expression. That an analogous minigenome assay established for Nipah virus, a related member of the paramyxovirus family, was not sensitive to compound 16677 underscores the target specificity of the inhibitor and further emphasizes that the compound targets viral rather than cellular components.

It is also noteworthy that the $IC_{50}$ concentrations of compound 16677 were on average about 25-times higher in the minigenome assay than against the different MV isolates. This likely reflects the approximately 24-fold difference in length between the reporter gene and the viral genome.

The experimental data demonstrate that inhibition by compound 16677 is fully reversible. When the target is present, bound and free compound must therefore be in an equilibrium, which is determined by compound binding and dissociation rates. In this scenario, longer template sequences, requiring more polymerization cycles, may likely provide more opportunity for interference when compound concentrations decrease, resulting in the lower $IC_{50}$ values determined for compound 16677 against live virus.

The functional characterization of the compound 16677 identified by the methods of the present disclosure has therefore demonstrated that the compound represents the first-in-class of novel, highly potent non-nucleoside inhibitors of the MV polymerase complex. While several nucleoside inhibitors of MV are known, these typically show at least 10 to 100-fold lower potency than compound 16677 with $IC_{50}$ concentrations typically in the micromolar range.

The present disclosure also encompasses variants and derivatives of compound 16677. Especially advantageous compounds for use as effective anti-measles therapeutic agents are compounds such as, but not limited to, structures as shown in FIGS. 11-13B. A particularly active compound, with a low level of cytotoxicity is compound AS-136A having the formula:

The methods of the present disclosure, including the high throughput screening methods, are also advantageous for the screening of potential therapeutic agents effective against infections of other target and clinically relevant members of the paramyxovirus family such as the recently emerged, highly pathogenic henipaviruses (Eaton, et al., (2006) *Nat. Rev. Microbiol.* 4(1), 23-35; Wang et al., (2001) *Microbes Infect.* 3(4), 279-287). In this scenario, they prepare the path for a better mechanistic understanding of these viruses and the development of novel therapeutic strategies against pathogens for which no vaccines are currently available.

Accordingly, one aspect of this disclosure are methods for identifying a compound for inhibiting the proliferation of a paramyxovirus, comprising: infecting mammalian cells with a recombinant paramyxovirus capable of expressing a viral polypeptide; contacting a first culture of the infected mammalian cells with a test compound; and determining the amount of expression of the viral polypeptide by the first cell culture; and the amount of expression of the viral polypeptide by a second cell culture not in contact with the test compound, whereby a reduction in the viral polypeptide expression in the first cell culture relative to that in the second cell culture indicates that the test compound is capable of inhibiting the expression of a paramyxovirus gene.

In embodiments of the methods of the disclosure, the inhibition of the expression of the paramyxovirus gene may correlate with the ability of the test compound to inhibit proliferation of a paramyxovirus.

In embodiments of the methods of the disclosure, the inhibition of the proliferation of the paramyxovirus gene is not by inhibiting the entry of the virus into a host cell or assembly of intact viral components in the cell.

In one embodiment of the methods of the disclosure, the recombinant paramyxovirus is a recombinant measles virus.

In embodiments of the methods of the disclosure the expressed viral polypeptide can be operably linked to an indicator polypeptide that may be an enhanced fluorescence protein operably linked to a paramyxovirus-specific polypeptide.

In one embodiment of the disclosure, the indicator polypeptide may be an enhanced green fluorescence protein, and the amount of viral polypeptide expression is determined by measuring an amount of fluorescence.

In embodiments of this aspect of the disclosure the paramyxovirus may be a measles virus.

Other embodiments of the methods of the disclosure, the methods may further comprise: obtaining a plurality of first mammalian cell cultures infected with a recombinant paramyxovirus; and contacting each first cell culture with at least one test compound of a plurality of compounds.

The disclosure, therefore, also encompasses a high throughput method for identifying a compound for inhibiting the proliferation of a paramyxovirus, comprising: infecting mammalian cells with a recombinant paramyxovirus capable of expressing a viral polypeptide; contacting a first culture of the infected mammalian cells with a test compound; and determining the amount of expression of the viral polypeptide by the first cell culture; and the amount of expression of the viral polypeptide by a second cell culture not in contact with the test compound, whereby a reduction in the viral polypeptide expression in the first cell culture relative to that in the second cell culture indicates that the test compound is capable of inhibiting the expression of a paramyxovirus gene. In this aspect of the disclosure, in one embodiment, the recombinant paramyxovirus may be a recombinant measles virus and the paramyxovirus is a measles virus.

Another aspect of the disclosure is a composition capable of inhibiting the proliferation of a paramyxovirus, wherein the compound comprises a sulfonamide group.

Figure 2C:
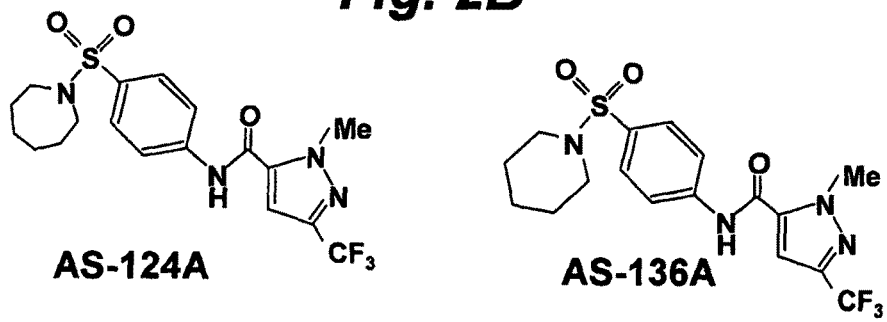
FIG. 2C illustrates the chemical structures of two illustrative compounds identified by screening and effective against in vitro (compound 16677 and AS-136A) and in vivo (AS-136A) mammalian cell infections by measle virus.
Figure 3A:
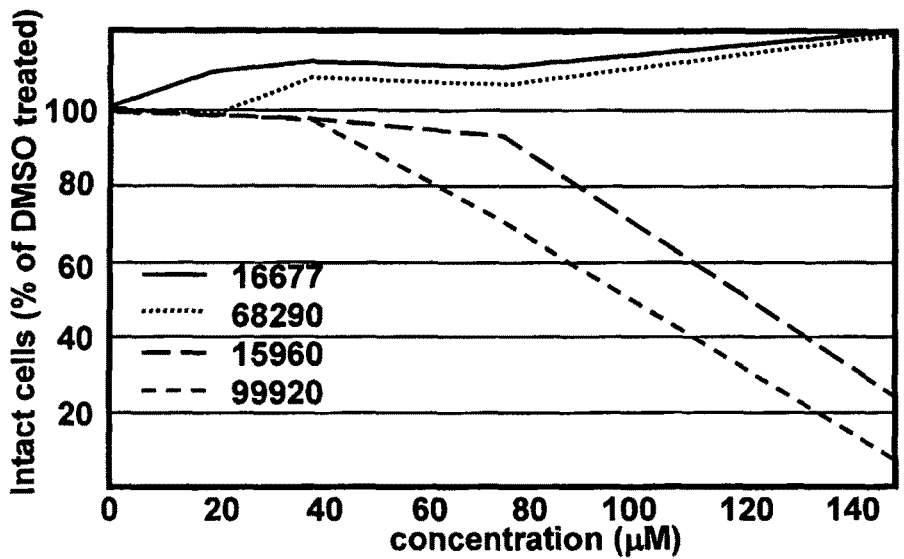
FIG. 3A illustrates that cytotoxic concentrations of all four hit candidates exceed concentrations used for hit discovery by quantification of the extent of chemical lysis of cells incubated in the presence of compound. Values reflect the percentage of signal intensity as compared with cells incubated in the presence of DMSO. Averages of four replicates are shown and error bars represent standard deviations.
Figure 3B:
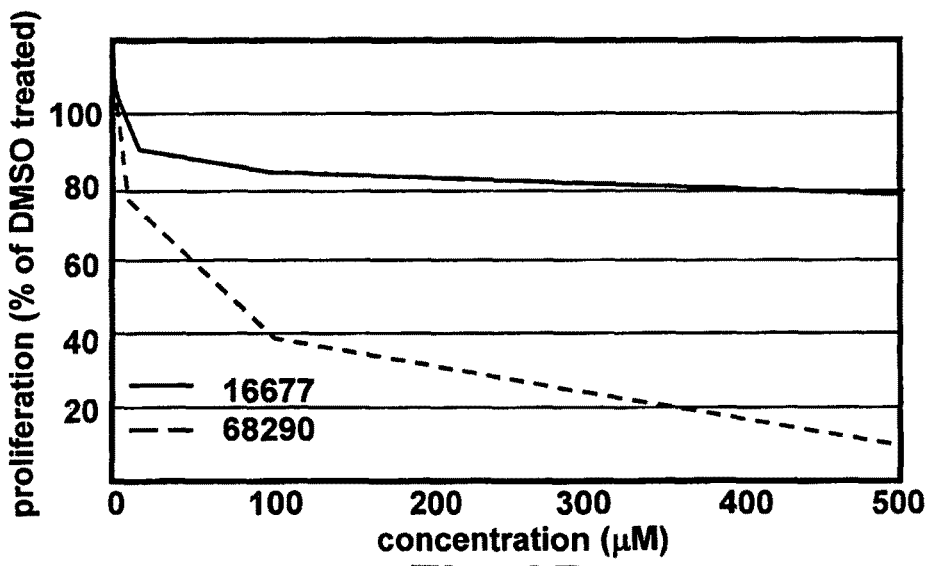
FIG. 3B illustrates that cytotoxic concentrations of all four hit candidates exceed concentrations used for hit discovery by quantification of proliferation activity of cells incubated in the presence of compound. The number of live cells was determined 30 hours post compound addition. Values indicate the percentage of live cells as compared with DMSO-treated controls. Averages of three experiments and standard deviations are shown.
Figure 4A:
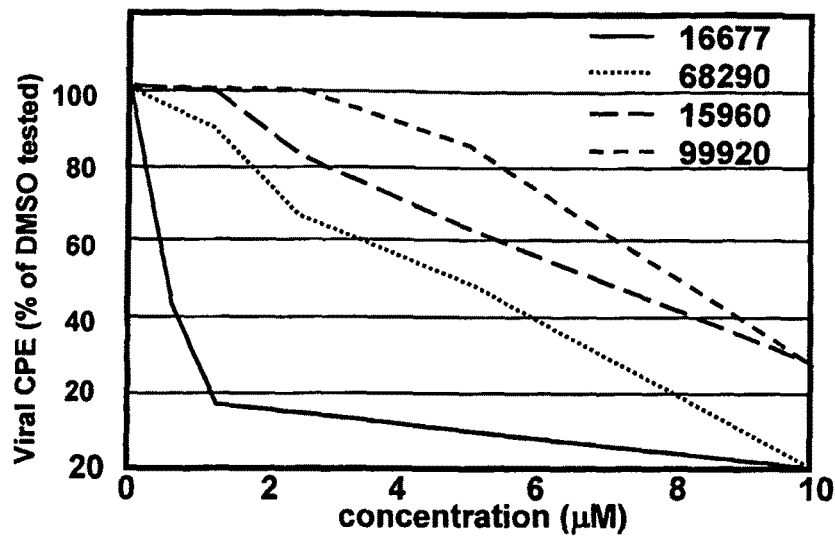
FIG. 4A illustrates manual secondary assays confirm anti-MV activity of the four hit candidates by quantitative cytopathicity assay to determine sensitivity of MV-Edm to the compounds. Values represent averages of four replicates and are expressed as percentage of the cytopathic effect (CPE) observed in DMSO-treated control infections. Standard deviations are shown.
Figure 4B:
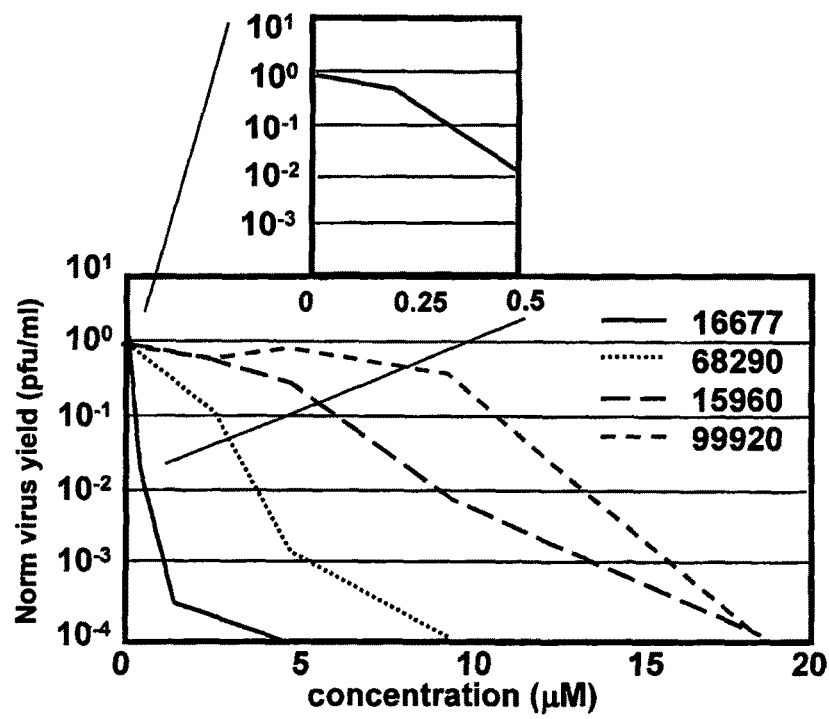
FIG. 4B illustrates manual secondary assays confirm anti-MV activity of the four hit candidates by virus yield assay to determine the reduction of virus loads. Cells were infected with MV-Edm in the presence of different compound concentrations and titers of cell-associated viral particles determined by $TCID_{50}$ titration 36 hours post infection. Titers were normalized for DMSO-treated control infections to facilitate comparison of different experiments. $IC_{50}$ concentrations of the different compounds range from approximately 0.24 (insert) to 7.7 µM. Average values of two experiments are shown.

Embodiments of this aspect of the disclosure include, but are not limited to, the structures illustrated in FIGS. 2B and 2C.

Embodiments of this aspect of the disclosure further include, but are not limited to, compounds having the structures as illustrated in FIG. 11.

One embodiment of this aspect of the disclosure may also be 1-methyl-3-(trifluoromethyl)-N-[4-(pyrrolidinylsulfonyl)-phenyl]-1H-pyrazole-5-carboxamide (designated compound 16677) having the structure illustrated in FIG. 2B.

Another embodiment of this aspect of the disclosure may also be 1-methyl-N-(4-(piperidin-1-ylsulfonyl)phenyl)-3-(trifluoromethyl)-1H-pyrazole-5-carboxamide (designated AS-136A) having the structure illustrated in FIG. 2C.

Other embodiments of the disclosure include, but are not limited to, the structures as shown in FIG. 12B.

Yet another aspect of the disclosure are methods of inhibiting the proliferation of a paramyxovirus in a mammalian cell comprising administering to the cell an effective amount of at least one paramyxovirus inhibitor composition, wherein the paramyxovirus inhibitor is a compound having the structure shown in FIG. 2C.

One embodiment of the disclosure comprises administering the effective dose to a recipient animal or human for the treatment of a paramyxovirus infection such as, but not only, a measles infection.

In one embodiment of this aspect of the disclosure, the administered composition comprises the compound 16677 shown in FIG. 2B, compound AS-124A or compound AS-136A as shown in FIG. 2C.

In one embodiment of the disclosure, the administered composition may comprise compound 16677 shown in FIG. 2B Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein. All publications, patent applications, patents, and other references mentioned herein are incorporated by reference in their entirety. In addition, the materials, methods, and examples are illustrative only and are not intended to be limiting.

The following examples are provided to describe and illustrate, but not limit, the claimed disclosure. Those of skill in the art will readily recognize a variety of non-critical parameters that could be changed or modified to yield essentially similar results.

EXAMPLES

Example 1

Cell Culture, Transfection, and Production of MV Stocks.

All cell lines were maintained at 37° C. and 5% $CO_2$ in Dulbecco's modified Eagle's medium (DMEM) supplemented with 10% fetal bovine serum (FBS), penicillin, and streptomycin. Vero-SLAM cells, derived from Vero (African green monkey kidney epithelial) cells (ATCC CCL-81) and stably expressing human SLAM/CD150w, Vero-dogSLAM cells (Seki et al., (2003) *J Virol* 77(18), 9943-9950) stably expressing dog SLAM, and BSR T7/5 cells (Buchholz et al., (1999) *J Virol* 73(1), 251-259) stably expressing T7 polymerase were incubated at every third passage in the additional presence of G-418 (Geneticin) at a concentration of 100 µg/ml. Lipofectamine 2000 (Invitrogen) was used for transient transfection experiments according to the manufacturer's instructions. To prepare virus stocks, cells were infected at a multiplicity of infection (MOI) of 0.001 plaque-forming units (pfu)/cell and incubated at 37° C. Cells were scraped in OPTIMEM (Invitrogen), virus released by two freeze-thaw cycles, and titers determined by 50% tissue culture infective dose ($TCID_{50}$) titration according to the Spearman-Karber method (Spearman, C. (1908) *Br. J. Phsychol.* 2, 227-242) as previously described (Plemper et al., (2002) *J Virol* 76(10), 5051-5061). MV-Edmonston (MV-Edm) stocks were grown and titered on Vero cells, while for MV field isolates Vero-SLAM cells and for canine distemper virus (CDV) Vero-dogSLAM cells were used. All MV field isolates were originally derived from PBMC samples and the viruses were isolated and minimally passaged on SLAM-positive B95-a cells or Vero-SLAM cells.

Example 2

High Throughput Compound Screening.

For screening, Vero cells were seeded in 96-well microtiter plates at a density of 7,500 cells per well in 100 ml growth medium. After a four-hour incubation period at 37° C. and 5% $CO_2$, test compound was added in 1.0 μl/well doses (20 μM final concentration) with a Sciclone automated liquid handler system (Caliper, Mass.), followed by infection with rMV-eGFP (Ehrengruber et al., (2001) Mol. Cell. Neurosci. 17(5), 855-871) at an MOI of 0.25 pfu/ml in 100 ml serum-free medium. Final solvent (DMSO) concentrations were 0.5% at which no adverse effect on cell viability or virus growth could be detected in control samples.

Pilot experiments revealed minimal wall effects and little cross-fluorescence between wells of the microtiter plates, permitting usage of the full capacity of each plate. All virus stocks used for screening were subjected to dialysis against PBS to remove contaminating eGFP that has been synthesized during virus growth. Following a 64-hour incubation period at 37° C., green fluorescence indicating expression of viral proteins was quantified using an Analyst HT microplate reader (Molecular Devices).

To validate the assay, the MV fusion inhibitor AS-48 (Plemper et al., (2005) *Antimicrob. Agents Chemother* 49(9), 3755-3761) was added in an otherwise identical setting as a positive control, and z' values were calculated according to the formula $z'=1-(3\ SD_{(C)}+3\ SD_{(B)})/(Mean_{(C)}-Mean_{(B)})$, with C: control and B: background (Zhang et al., (1999) *J Biomol Screen* 4, 67-73). As first-pass test to exclude false-positive compounds, cytotoxicity was assessed microscopically for all wells that showed low fluorescence intensity and, for selected compounds, photo-documented at a magnification of 200×. The compound library used is a diversity set from ChemDiv (San Diego, Calif.).

Example 3

Chemical Synthesis of Compound 16677.

Figure 10:
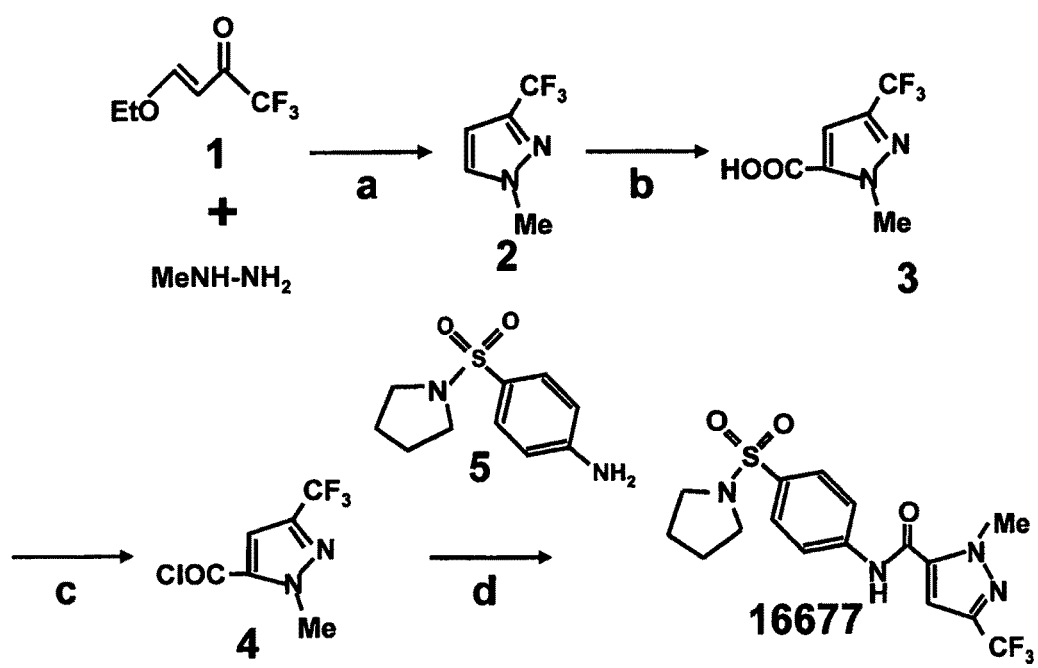
FIG. 10 illustrates synthesis of 1-methyl-3-(trifluoromethyl)-N-[4-(pyrrolidinylsulfonyl)-phenyl]-1H-pyrazole-5-carboxamide (compound 16677). Reagents: (a) MeOH, reflux; (b) n-BuLi/i-Pr2NH, then CO2; (c) (COCl)$_2$, DMF, CH2Cl2, 0° C.-rt; (d) py, CH$_2$Cl$_2$, rt.

For synthesis of compound 16677, 1-methyl-3-trifluoromethyl-5-pyrazolecarboxylic acid 3 (Scheme 1, FIG. 10) was prepared from commercially available compound 1 as previously described (Schlosser et al., (2002) *Eur. J. Org. Chem.* 2002(17), 2913-2920). Compound 3 (820 mg, 4.2 mmol) in dichloromethane (10 ml) was treated with oxalyl chloride (2.0 M in $CH_2Cl_2$, 8.5 mmol, 4.2 ml) and a catalytic amount of DMF. The reaction mixture was incubated at room temperature for 5 hours. Evaporation of solvent delivered yellow acyl chloride 4 in quantitative yield.

A portion of the latter in dichloromethane (0.55 mmol) was added to a cold solution of 4-amino-prolidinyl sulfonamide 5 (113.1 mg, 0.5 mmol), pyridine (48 μl, 0.6 mmol) in dichloromethane (2 ml). The reaction mixture was warmed to room temperature (18 hours), poured into dilute hydrochloric acid (1N), extracted with dichloromethane (3×15 ml) and dried over anhydrous $Na_2SO_4$. The product was purified by chromatography using hexane/ethyl acetate (3:1) to obtain compound 16677 as a while powder (110.2 mg, 55% yield). $^1H$ NMR (400 MHz, $CDCl_3$) δ1.76-1.80 (4H, m), 3.24-3.27 (4H, m), 4.28 (3H, s)), 7.75-7.77 (2H, m), 7.84-7.87 (3H, m). HRMS calculated for $C_{16}H_{17}F_3N_4O_3S$, 402.0974, found 403.1044 (M+1). Anal. calculated for $C_{16}H_{17}F_3N_4O_3S$: C, 47.76; H, 4.26; N, 13.92. found C, 47.71; H, 4.23; N, 13.81.

Subsequent to hit identification and initial confirmation, the synthetic sample was used for all experiments.

Example 4

Quantification of Compound Cytotoxicity.

Two independent assays, a non-radioactive cytotoxicity assay (Promega) and a trypan-blue exclusion assay, were employed to determine cytotoxicity of compounds. For the cytotoxicity assay, 12,000 cells per well in a 96-well plate format were incubated at 37° C. for 24 hours in four replicates per concentration tested in the presence of a range of compound concentrations in 2-fold dilutions (150 μM highest). Conversion of a tetrazolium salt (INT) into a colored formazan product by cellular lactate dehydrogenase released into the culture supernatants was then measured at 490 nm using a BioRad plate reader. Values were calculated according to the formula [% viability=100−((experimental−background)/ (maximum−background)*100)].

For the trypan-blue exclusion assay, $2\times10^5$ cells per well were seeded in a 6-well plate format and incubated at 37° C. for 30 hours in three replicates per concentration tested in the presence of a range of compound concentrations in 5-fold dilutions (500 μM highest). Cells were then detached from culture dishes, aliquots incubated with trypan-blue solution for 15 minutes at room temperature, and the number of viable cells counted using a hemacytometer.

Example 5

Dose-Response Inhibition Curves Based on Suppression of Virus-Induced Cytopathicity.

As a straightforward confirmatory assay to determine the antiviral activity of hit candidates, suppression of virus-induced cytopathicity by the compound was assessed as previously described (Plemper et al., (2005) *Antimicrob Agents Chemother* 49(9), 3755-3761; Sun et al., (2006) *J Med Chem* 49(17), 5080-5092). Briefly, cells were infected in four replicates per concentration in a 96-well plate format with rMV-Edm at an MOI of 0.4 pfu/cell in the presence of a range of compound concentrations in two-fold dilutions (18.75 μM highest). At 96 hours post-infection, virus-induced cytopathicity was quantified using a proliferation assay (Promega) and results calculated according to the formula [% virus-induced cytopathicity=100−(experimental−background)/(maximum−background)*100], where "maximum" constitutes mock-infected cells and "background" media-only controls. Plotting of % virus-induced cytopathicity values as a function of the compound concentration allowed the calculation of 50%-effective ($EC_{50}$: virus-induced cytopathicity reduced by 50%) concentrations.

Example 6

Dose-Response Inhibition Curves Based on Virus Yields.

To generate virus yield-based dose-response curves, $4\times10^5$ cells per well were infected in a 6-well plate format with rMV-Edm, MV field isolates, CDV, or human parainfluenza-virus type 2 (hPIV2) as specified at an MOI=0.1 pfu/cell in the presence of a range of compound concentrations in two-fold dilutions (75 μM highest) or equivalent volumes of solvent (DMSO) only, and incubated in the presence of compound at 37° C. For assessment of clinical MV isolates, compound was added in 3-fold dilutions (37.5 μM highest). Thirty-six hours post-infection, cell-associated viral particles were harvested and titered as described above. Plotting virus titers as a function of compound concentration allowed the calculation of $IC_{50}$ concentrations, at which virus yields are 50% of DMSO-treated controls.

Example 7

Compound Specificity.

To determine compound specificity, $4\times10^5$ cells in a 6-well plate format were infected in serum-free growth medium at an MOI of 0.1 or 0.5 pfu/cell as specified in the presence of a range of compound 16677 concentrations in 4-fold dilutions (12.5 µM highest). Bovine serum albumin (BSA) was added to some samples at a final concentration of 10 mg/ml. When virus-induced cytopathicity in DMSO control samples reached approximately 75%, the complete series was harvested, titers of cell-associated viral particles determined by $TCID_{50}$ titration and $IC_{50}$ concentrations calculated for each series.

Example 8

Compound Stability.

To assess compound stability under physiological conditions, inhibitor compound 16677 was dissolved in growth medium (15 µM final concentration) and incubated at 37° C. and physiological pH for different time intervals (24 hours longest). Control samples contained equal amounts of DMSO and were likewise incubated for 24 hours. Subsequent to pre-incubation, MV was added to the compound aliquots and the mixtures transferred to $4\times10^5$ target cells seeded in a 6-well plate format (resulting MOI=0.1 pfu/cell). Thirty-six hours post-infection, cell-associated viral particles were harvested and virus titers determined by $TCID_{50}$ titration.

Example 9

Transient Fusion-Inhibition Assays.

To assess the ability of compound 16677 to inhibit cell-to-cell fusion induced by transiently expressed MV glycoproteins, a previously established assay was employed (Plemper et al., (2005) *Antimicrob Agents Chemother* 49(9), 3755-3761). Briefly, $6\times10^5$ cells per well were transfected in a 6-well plate format with 4 µg plasmid DNA each encoding MV-H and F genes, and cells transferred 4 hours post-transfection to 96-well plates containing compounds compound 16677 or AS-48 in a range of concentrations in two-fold dilutions (150 µM highest). Fusion activity was assessed microscopically 48 hours post-transfection and the extent of cytotoxicity as a consequence of extensive syncytium formation quantified according to the formula [% cytotoxicity= (experimental-background)/(maximum-background)*100] using the cytotoxicity assay (Promega) described above. For some experiments, cells were photo-documented 24 hours post-transfection.

Example 10

Dissociation Assays.

Viral particles ($4\times10^4$ pfu, equaling an MOI=0.1 pfu/ml) were mixed with compound 16677 (final concentration 15 µM) dissolved in phosphate buffered saline (PBS). After 10-minute incubation at 37° C. to allow compound binding, samples were either subjected to dialysis against PBS (molecular weight cut off=75 kDa, dilution factor 100,000×, 4° C., 10 hours) or incubated for 10 hours at 4° C. without dialysis. Control samples were treated with DMSO-only and subjected to dialysis. All samples were then transferred to $4\times10^5$ target cells seeded in a 6-well plate, cell-associated viral particles harvested 36 hours post-infection and viral titers determined by $TCID_{50}$ titration.

Example 11

Virus Entry Assays.

For entry experiments, viral particles (MOI=0.5) were absorbed to $4\times10^5$ target cells in a 6-well plate format at 4° C. in the presence of 10 µM compound 16677 or equal amounts of DMSO for one hour. Cells were then shifted to 37° C. for 30 minutes, followed by inactivation of adsorbed, extracellular virions by a 2-minute acid treatment (40 mM sodium citrate, 10 mM KCl, 135 mM NaCl, pH 3.0) at 25° C. as previously described (37,39,49). Subsequent incubation for 30 hours at 37° C. in the presence or absence of 10 µM compound 16677 as specified was followed by determination of cell-associated virus titers by $TCID_{50}$ titration.

Example 12

Time of Compound Addition Assays.

Cells ($3\times10^5$/well in a 12-well plate format) were infected with MV at an MOI=1.0 pfu/ml and compounds compound 16677 (final concentration 15 µM) or AS-48 (final concentration 75 µM) added at the indicated time points. Control cells were infected in the presence of equal amounts of DMSO. Twenty hours post-infection, when virus-induced cytopathicity exceeded 90%, cell-associated viral particles were harvested and subjected to $TCID_{50}$ titration.

Example 13

Minireplicon Assays.

BSR T7/5 cells ($5\times10^5$ per well in a 6-well plate format) were transfected with plasmid DNAs encoding MV-L (0.24 µg), MV-N (0.94 µg) or MV-P (0.29 µg) and 2 µg of the MV chloramphenicol (CAT) minigenome reporter plasmid (Sidhu et al., (1995) *Virology* 208(2), 800-807). For analysis of Nipah virus polymerase activity, cells were transfected with plasmid DNAs encoding Nipah virus L (0.4 µg), N (1.2 µg) or P (0.8 µg) proteins and 3.5 µg of the Nipah CAT reporter plasmid as previously described (Halpin et al., (2004) *J Gen Virol* 85(Pt 3), 701-707). Control wells included identical amounts of reporter and helper plasmids but lacked the plasmids harboring the respective L gene. Two hours post-transfection, compound 16677 was added in a range of concentrations in three-fold dilutions (30 µM highest), while some wells received compound AS-48 or equal amounts of DMSO for comparison. Thirty-eight hours post-transfection, cells were lysed and CAT concentrations in the lysates determined using a CAT-ELISA assay system (Roche).

Example 14

In Vitro Protein Transcription/Translation.

Rabbit reticulocyte lysates were mixed with 0.5 µg plasmid DNA encoding MV F under the control of the T7 promoter (pT7-MV F), 20 µCi [$^{35}$S]-methionine, and compound 16677 (final concentration 50 µM) or equal volumes of DMSO. Samples were incubated at 30° C. for 90 min, mixed with urea buffer (200 mM Tris, pH 6.8; 8 M urea; 5% SDS; 0.1 mM EDTA; 0.03% bromphenolblue; 1.5% dithiothreitol), and fractionated on 12% polyacrylamide gels. Dried gels were exposed to Kodak XAR films.

Example 15

Development of a Primary Assay Suitable for Automated Screening of MV Antivirals.

To identify novel MV inhibitor candidates, we have developed a protocol for the automated screening of compound libraries for their activity against live MV, using the previously described MV entry inhibitor, AS-48, as a positive control. The assay relies on a recombinant MV that harbors eGFP as an additional transcription unit (rMV-eGFP) (Ehrengruber et al., (2001) *Mol Cell Neurosci* 17(5), 855-871) and detects eGFP-mediated fluorescence as an indicator for expression of the viral genome. To remove traces of eGFP that were synthesized during virus stock production from the inoculum, all virus preparations were subjected to dialysis against PBS prior to use in this assay. This procedure completely eliminated background fluorescence from the inoculum while maintaining more than 95% of input infectivity as determined by $TCID_{50}$ titration (data not shown).

Due to positioning of the eGFP-encoding transcription unit in the 5'-prime position of a positive strand cDNA copy of the viral genome, every infectious cycle results in eGFP synthesis prior to expression of the viral proteins. Consequently, our assay should predominantly identify compounds that interfere with vial entry or viral gene expression and genome replication, whereas inhibitors of late events of the viral live cycle such as particle assembly and release are less likely to be discovered. A low fluorescence signal in this assay thus indicates a reduced rate of viral genome expression. This may either reflect a hit candidate, or a highly cytotoxic compound that yields a false-positive readout. Since the Emory in-house compound library used for this screening exercise had not been prescreened to exclude entries with strong general cytotoxicity, we anticipated that a considerable number of compounds would indeed show substantial cytotoxicity. Cell viability was therefore determined microscopically in a second step for all wells in which the automated system detected low fluorescence intensities.

When employing the MV entry inhibitor AS-48 to evaluate this assay, we observed a time-dependent increase in signal intensity reflecting virus growth and genome expression. At 64 hours post-infection, the signal to background ratio (S/B) reached 6.43 and the overall z' value was 0.8 (FIG. 1). For comparison, robust screening protocols typically yield z' values from 0.5 to 1, indicating the broad suitability of an assay for automated screening (Zhang et al., (1999) *J Biomol Screen* 4, 67-73). These results therefore recommended our protocol as a suitable strategy for HTS-based hit identification.

Example 16

Library Screening Yields Four Sulfonamide Hit Candidates.

This assay to the automated screen of 34,000 compounds of an Emory library. This process yielded 12 potential hits that reduced GFP fluorescence to background levels and showed low cytotoxicity when wells were microscopically assessed. Retesting of these molecules in the same assay reduced the number of reproducible hits to four compounds (photographic documentation is shown in FIG. 2A), thus equating to a hit identification rate of approximately 0.01%. The structures of the four hit compounds are depicted in FIG. 2B. Each of these compounds incorporates a sulfonamide unit.

Example 17

Secondary Confirmatory Assays Identify Compound 16677 as the Most Potent Hit.

To compare antiviral activity and assess whether these compounds represent true hits that warrant hit-to-lead development, each was subjected to several independent secondary assays. We first quantified inherent cytotoxicity of the four compounds using a colorimetric cytotoxicity assay that measures the amount of cellular lactate dehydrogenase released into the culture supernatants of cells incubated in the presence of compound (Barltrop et al., (1991) *Bioorg. & Med. Chem. Lett.* 1(11), 611-614). Candidate compounds 99920 and 15960 revealed 50% cytotoxic concentrations ($CC_{50}$) of 100 and 120 μM respectively, while compounds 68290 and compound 16677 showed no detectable toxicity at 150 μM, the highest concentration examined (FIG. 3A).

These experiments were complemented for compounds 68290 and compound 16677 by an independent trypan-blue exclusion assay that determines the number of viable cells after growths in the presence of compound and thus the effect of the inhibitor on cell proliferation rates and viability. For compound 16677, numbers of live cells reached approximately 80% of solvent-treated controls after incubation in the presence of compound concentrations as high as 500 μM, while for compound 68290 a 50% reduction of the number of live cells was observed at approximately 75 μM (FIG. 3B).

Since the $CC_{50}$ values of all candidate compounds substantially exceeded the concentrations used in the primary HTS assay (25 μM), all four were subjected to a confirmatory assay that measures the suppression of the MV-inherent cytopathic effect (CPE) by an active inhibitor (Plemper et al., (2005) *Antimicrob Agents Chemother* 49(9), 3755-3761; Sun et al., (2006) *J Med Chem* 49(17), 5080-5092). In vitro, extensive syncytia formation is characteristic of infection of receptor-positive cells with MV. This is followed by detachment and disintegration of the resulting giant cells when they become mechanically unstable, usually three to four days post-infection depending on the virus strain and multiplicity of infection. The resulting loss in cell-proliferation activity can be quantified in a cell-proliferation assay as surrogate readout for the amount of MV-induced CPE. When subjected to this assay, all four putative hits revealed a dose-dependent reduction of viral CPE with 50% effective concentrations ($EC_{50}$) ranging from 8 to 0.8 μM (FIG. 4A), translating into preliminary, CPE-based selectivity indexes ($SI=CC_{50}/EC_{50}$) from 14 to >187 for compound 16677, the most potent inhibitor in this assay. These results thus confirm the observations of the primary HTS screen.

Since all hit candidates show a dose-dependent suppression of MV-mediated CPE, all four compounds were subjected to a second confirmatory assay that measures the reduction of virus yields by an inhibitor. Using as the viral target recombinant MV-Edm, which was also employed for the original HTS screen, compound 16677 was again found to have the greatest antiviral potency with an $IC_{50}$ concentration of approximately 240 nM (FIG. 4B, insert), translating to an SI index of >625. The other three candidates showed $IC_{50}$ values of 1.3 μM (99920), 3.4 μM (15960), and 7.7 μM (68290) (FIG. 4B). Although the CPE-based assay constitutes a robust first-pass tool for follow-up screening, it should be noted that the reduction in virus loads as determined in this second assay is the most relevant parameter. Taken together, all secondary assays recommended compound 16677 as a particularly promising candidate MV inhibitor.

Compounds incorporated in HTS libraries, particularly those dissolved in DMSO, are known to degrade and/or rearrange upon prolonged storage (Talaga, P. (2004) *Drug Discovery Today* 9, 51-53). It is therefore essential to confirm key hit structures by independent synthesis. This not only assures chemical and structural integrity, but also provides pure samples for further biological characterization. The pure synthetic sample proved equally effective against MV as the HTS sample.

Example 18

Compound 16677 is a Well-Behaved, Target-Specific MV Inhibitor.

To determine the developmental potential of candidate compound 16677, we next evaluated its target specificity and biophysical properties. A common obstacle repeatedly encountered in HT or virtual screens is the identification of promiscuous compounds, which are characterized by poor target specificity and noncompetitive inhibition. These are found typically in the low micromolar range due to absorption to compound aggregates (McGovern et al., (2002) *J Med Chem* 45(8), 1712-1722; McGovern et al., (2003) *J Med Chem.* 46(8), 1478-1483). While this is more frequently encountered in protein-based rather than cell-based assays, we subjected candidate compound 16677 to two assays that are reportedly sufficient to differentiate well-behaved from promiscuous inhibitors (McGovern et al., (2002) *J Med Chem.* 45(8), 1712-1722; McGovern et al., (2003) *J Med Chem* 46(8), 1478-1483). For these and all following experiments, the MV field isolate Anchorage (MV-Anc) was employed, since this strain was found to be highly sensitive to compound 16677 (see below).

Figure 5A:
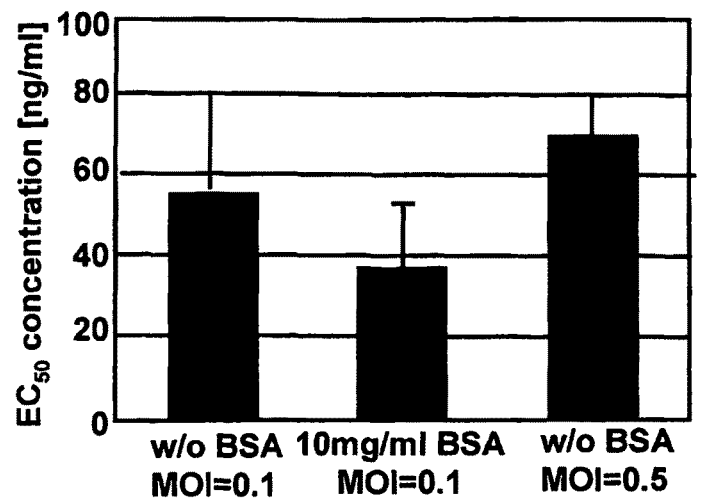
FIG. 5A illustrates that compound 16677 is a well-behaved, target-specific MV inhibitor in that unrelated protein material or variation of the amount of target molecules does not affect compound 16677 activity. Virus-yield based dose response curves as shown in FIG. 4B were generated for compound 16677 upon infection of cells with MV-Anc in the absence of bovine serum albumin (BSA), in the presence of BSA, and after infection with a 5-fold higher virus inoculum. Values represent average $IC_{50}$ concentrations of two experiments.

The first assay measures the effect of additional inert protein such as bovine serum albumin (BSA) on compound activity, and the second monitors the outcome of an increase in the amount of available target. BSA is thought to compete with the target protein for non-specific binding to compound aggregates. An increase in the amount of target molecules quickly saturates the absorption capacity of these aggregates. In either case, promiscuous compounds characteristically show a sharp drop in activity reflected by increased $IC_{50}$ concentrations, while $IC_{50}$ values of well-behaved inhibitors are essentially unaffected. When $IC_{50}$ concentrations were determined for compound 16677 after incubation of infected cells in the presence and absence of 10 mg/ml BSA, or after infection with a five-fold higher virus inoculum, no significant differences were observed (FIG. 5A), indicating a well-behaved MV inhibitor.

Figure 5B:
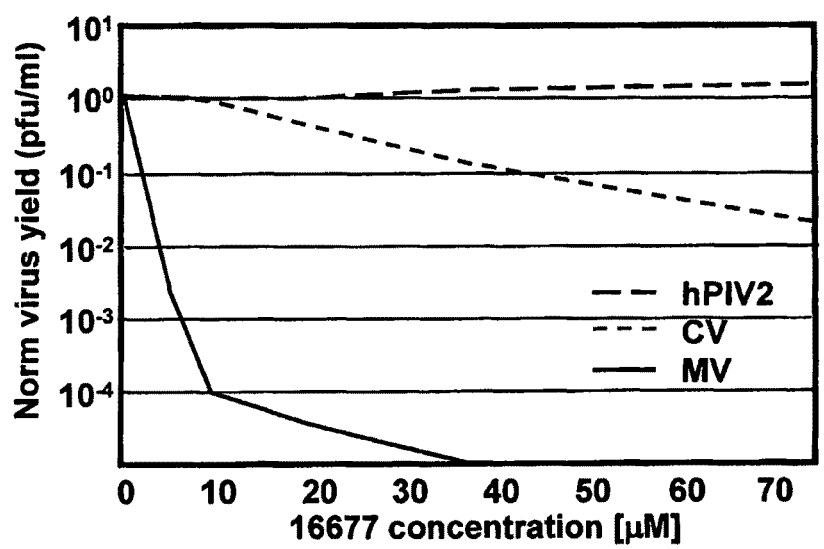
FIG. 5B that illustrative compound 16677 is highly MV specific. Virus-yield based dose-response curves were generated for MV, closely related canine distemper virus (CDV), and more distantly related human parainfluenzavirus type 2 (hPIV2). Titers were normalized for DMSO-treated control infections to facilitate comparison of different experiments. Average values of two experiments are shown.

Assessment of activity of compound 16677 against two related members of the paramyxovirus family, canine distemper virus (CDV) and human parainfluenzavirus type 2 (hPIV2), corroborated these findings. Like MV, CDV belongs to the genus morbillivirus and both viruses share approximately 61% protein identity, while hPIV2 is more distantly related and shows only 21% protein identity with MV. When dose-response curves were generated for these viruses, compound 16677 yielded $IC_{50}$ values of 28 μM against CDV, and hPIV2 was entirely uninhibited at 75 μM, the highest concentration examined in this assay FIG. 5B). These data thus demonstrate high specificity of compound 16677 for MV and to a lesser degree for intimately related CDV, and argue against a nonspecific mechanism of activity. They also confirm the results of the initial cytotoxicity assay, since general cytotoxicity, if contributing to the biological activity of the compound, should extend equally to CDV and hPIV2.

Example 19

Inhibitory Activity is Stable Under Physiological Conditions, and Compound 16677 Binding is Reversible.

Figure 6A:
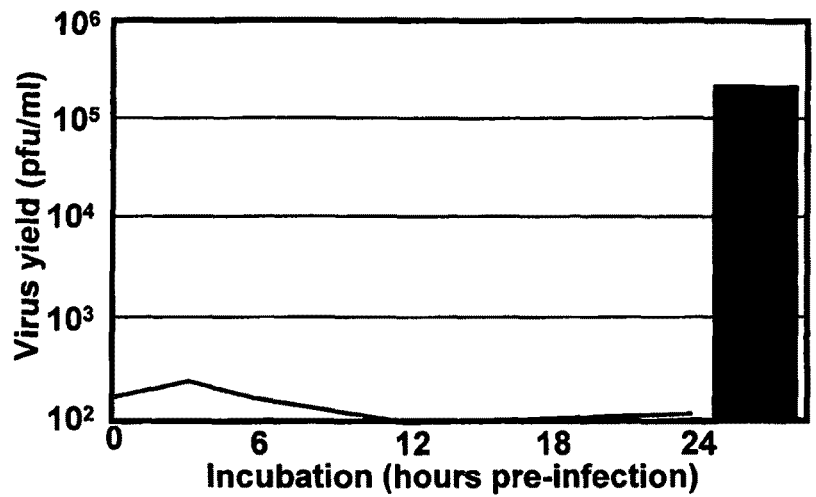
FIG. 6A illustrates compound 16677 is stable at physiological conditions and inhibition is reversible. Compound dilutions in growth medium (final concentration 15 µM) were pre-incubated at 37° C. for the indicated time periods, followed by transfer to cells and infection with MV-Anc. For control (untreated), equal dilutions of DMSO in growth medium were pre-incubated for 24 hours. Values represent titers of cell-associated viral particles determined 36 hours post-infection through $TCID_{50}$ titration. Averages of two experiments are shown.

A long half-life of antiviral activity under physiological conditions and absence of chemical reactivity are desirable properties of inhibitor candidates that warrant further development. To assess its stability under physiological conditions, compound 16677 was pre-incubated in cell culture medium at 37° C. for different time periods ranging from 0 to 24 hours, followed by mixing with MV-Anc and infection of target cells. While virus grew efficiently in solvent only-treated control infections, no loss in antiviral activity of compound 16677 could be detected even after pre-incubation for 24 hours (FIG. 6A), indicating a favorable stability profile for this compound.

Figure 6B:
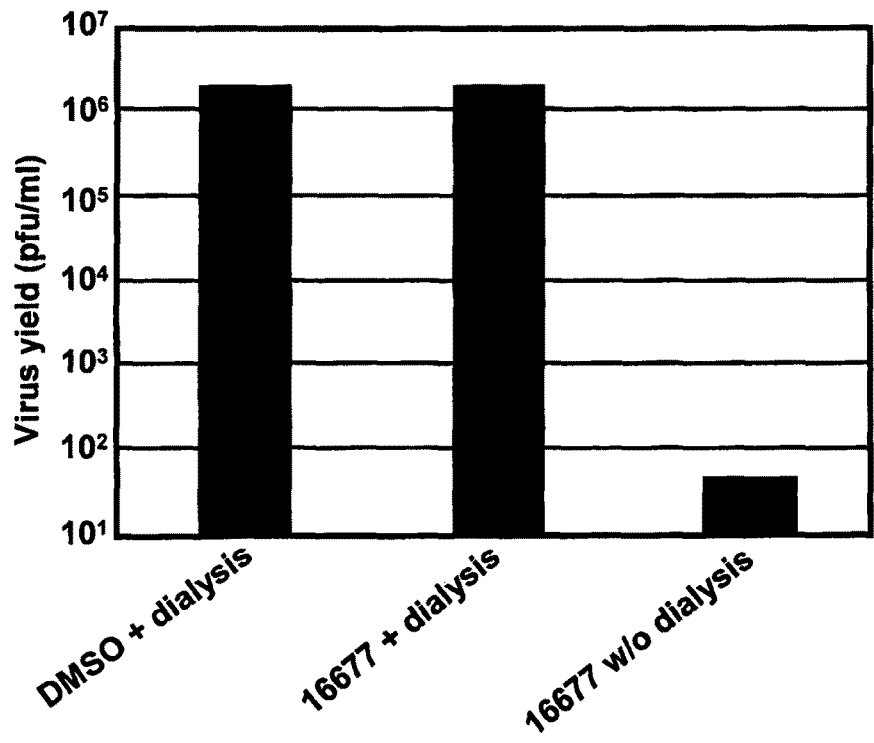
FIG. 6B illustrates that removal of compound 16677 through dialysis fully restores viral replication. Virus dilutions (equivalent of 0.1 MOI) were mixed with compound 16677 (final concentration 15 µM) and subjected to dialysis against phosphate buffered saline. Cells were subsequently infected with the mixtures and viral titers determined 36 hours post-infection by $TCID_{50}$ titration. Controls include DMSO treated virions and compound-treated samples maintained at the same conditions without (w/o) dialysis. Averages of two experiments are shown.

To explore whether the compound 16677 chemically reacts with its target or whether compound docking is reversible, MV aliquots were incubated with the compound in the absence of target cells for 10 minutes at 37° C., followed by dialysis at 4° C. with a molecular weight cutoff of 75 kDA, which ensures free diffusion of the compound but not the viral particles (total dilution factor of compound 100,000-fold). Controls included solvent-only treated particles that were similarly subjected to dialysis, and compound 16677-treated virus samples that were, instead of being dialyzed, held at 4° C. for the same time period. Subsequent infection of cells with the different virus samples and titration of infectious particles produced 30 hours post-infection revealed that the inhibitory activity of compound 16677 is completely ablated by dialysis prior to infection (FIG. 6B), indicating that compound docking is entirely reversible and not based on a chemical reaction of the inhibitor with the target.

Example 20

Potent Activity of 16677 Against Primary MV Isolates, Including an Isolate Resistant to an MV Entry Inhibitor.

To explore the potential value of candidate compound 16677 as a clinically relevant inhibitor of MV, we assessed its activity against a panel of primary MV isolates that represent several genotypes currently circulating worldwide. Importantly, this panel included the Sub-Saharan isolate of genotype B3, MV-Ibd, which we have previously found to be resistant to our series of MV entry inhibitors (Doyle et al., (2006) *J Virol* 80(3), 1524-1536). Depending on the genotype of the MV strain analyzed, calculated $IC_{50}$ values ranged from 31 to 140 nM for these isolates (FIG. 7). MV-Ibd was likewise efficiently inhibited by compound 16677, indicating that no cross-resistance exists between this compound class and the previously characterized MV entry inhibitors. All primary isolates tested were also more sensitive to compound 16677 than was the recombinant MV-Edm virus (genotype A), on which the original hit discovery was based. Importantly, viruses of genotype A have not been endemic in several decades, underscoring the therapeutic potential of the inhibitor class represented by compound 16677.

Example 21

Compound 16677 Targets a Post-Entry Step in the Viral Life Cycle.

Figure 8B:
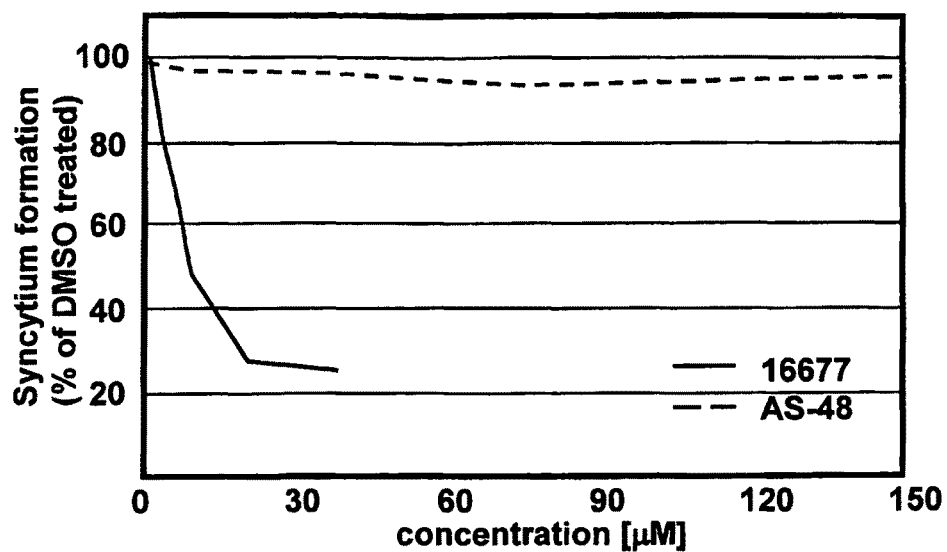
FIG. 8B illustrates that compound 16677 does not interfere with viral entry and is active late in the replicative cycle by quantification of syncytium formation of transfected cells treated as described in A. Values represent averages of four replicates and are expressed as percentage of syncytium formation observed for DMSO treated samples. Standard deviations are shown.

To gain insight into the mechanism of compound 16677 antiviral activity, we subjected the compound to an initial mechanistic characterization. Due to the nature of the HTS assay design, inhibitors identified in the context of this screen are less likely to block later events of the viral life cycle such as particle assembly (which would not affect eGFP expression), but are more likely to interfere with the function of the MV envelope proteins or the viral polymerase complex. We therefore first addressed the question whether membrane fusion and hence viral entry is inhibited by the compound. In the presence and absence of compound 16677, MV receptor-positive cells were transiently transfected with expression plasmids encoding the MV H and F envelope glycoproteins, and the extent of membrane fusion examined microscopically. Controls included transfected cells treated with the lead entry inhibitor AS-48, and compound 16677-treated cells that were infected with MV rather than plasmid transfected. In contrast to the strong inhibitory effect of AS-48, cell-to-cell fusion mediated by transiently expressed MV H and F proteins was entirely uninhibited by compound 16677 (FIG. 8A). Importantly, virus-mediated cytopathicity was fully suppressed by the compound, confirming specificity of the assay. Quantification of the envelope glycoprotein-induced cytopathicity and generation of dose-response curves for both compound 16677 and compound AS-48 confirmed these microscopic observations, since MV H and F protein-mediated cell-to-cell fusion was entirely uninhibited even at very high compound 16677 concentrations of 150 μM (FIG. 8B).

A viral entry assay was employed to assess whether the transient expression assay accurately reflects the conditions of virus infection. As demonstrated for several enveloped viruses (Kizhatil & Albritton, (1997) *J Virol* 71(10), 7145-7156), infectivity of MV particles is completely ablated by a brief pH 3.0 wash (37,39).

Figure 8C:
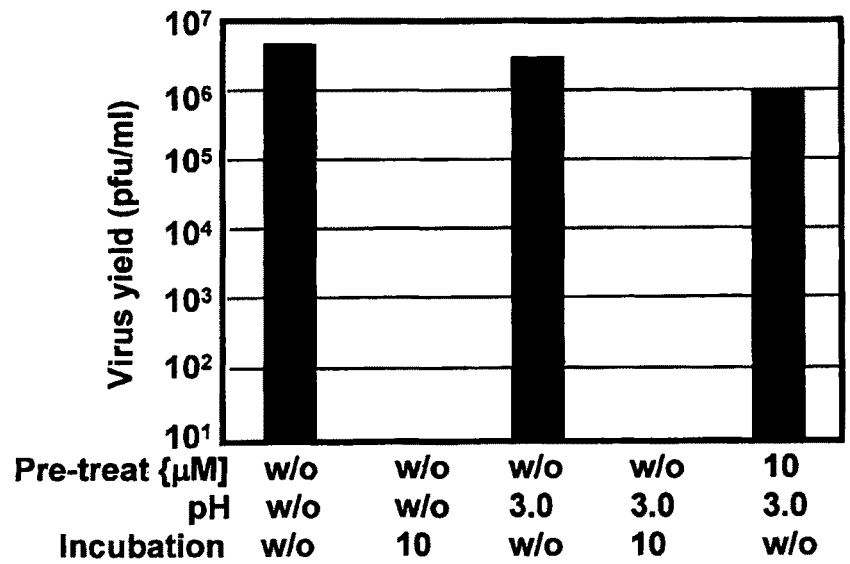
FIG. 8C illustrates that compound 16677 does not interfere with viral entry and is active late in the replicative cycle in that the presence of compound 16677 during absorption of virions to target cells does not render particles sensitive to neutralization by a pH 3.0 wash, indicating successful viral entry in the presence of compound. Virions were absorbed to target cells in the presence of DMSO or compound 16677, followed by pH 3.0 treatment to neutralize all particles that are in a pre-membrane fusion state and incubation in the presence of DMSO or compound 16677 as indicated. Yields of cell-associated viral particles were determined by $TCID_{50}$ titration. Average values of two experiments are shown.

Capitalizing on this, we absorbed MV particles (equivalent to an MOI of 0.5) to target cells at 4° C. in the presence or absence of compound 16677, followed by removal of unbound virus and a 30-minute incubation period at 37° C. to allow viral entry to proceed. Subsequently, some samples were subjected to a pH 3.0 wash to neutralize all particles that are in a pre-membrane fusion state, followed by incubation with or without compound and determination of virus yields. If compound 16677 interferes with viral entry, particle absorption in the presence of compound followed by low-pH treatment should result in a sharp drop in virus yields as exemplified by the previous analysis of members of the AS-48 entry inhibitor class in this assay (Plemper et al., (2004) *Proc Natl Acad Sci USA* 101(15), 5628-5633;

Plemper et al., (2005) *Antimicrob Agents Chemother* 49(9), 3755-3761). However, virus yields were only slightly affected by the pH 3.0 wash when compound 16677-treated samples were compared to DMSO-treated cells (FIG. 8C). Substantial reduction of virus yields by compound 16677 was only observed when the compound was present during the incubation period subsequent to the wash step, confirming its effectiveness (FIG. 8C). These findings thus fully corroborate the results of the transient cell-to-cell fusion assays and confirm that compound 16677 interferes with a post-entry step of the viral life cycle.

Figure 8D:
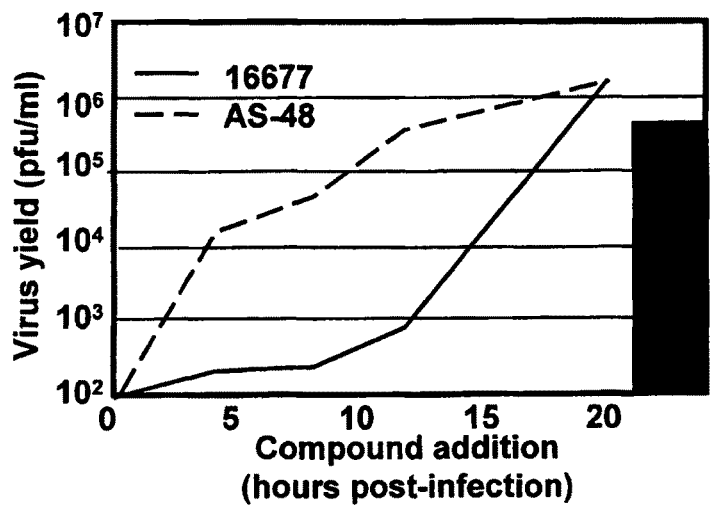
FIG. 8D illustrates compound 16677 does not interfere with viral entry and is active late in the replicative cycle in that antiviral activity of compound 16677 persists to late phases of a replicative cycle. The compound (final concentration 15 µM) was added at the indicated times post-infection to a one-step replicative cycle. Cell associated viral particles of compound treated samples and DMSO treated controls were harvested 20 hours post-infection and virus yields determined by $TCID_{50}$ titration. For comparison, infected cells were treated with the fusion inhibitor AS-48. Average titers of two experiments are shown.

To specify the time interval post entry in which the virus remains sensitive to inhibition by compound 16677, the effect of compound administration at different stages of the viral life cycle on replication efficiency was assessed. For this assay, viral growth was synchronized by infection of cells MV at an MOI of 1.0, thus essentially excluding secondary infections, and all samples were harvested 20 hours post-infection. Controls included infected cells treated with the entry inhibitor AS-48 or solvent-only treated infections. Even when added 12 hours post-infection, compound 16677 caused an approximately 99.9% reduction in virus yields, thus demonstrating high antiviral effectiveness (FIG. 8D). This was in contrast to compound AS-48, which, as expected, must be present at the time of viral entry to achieve full inhibition. Together, these data demonstrate that compound 16677 does not interfere with the viral entry machinery and point to a post-entry step as its mechanism of action.

Example 22

Compound 16677 Constitutes a New Class of MV Polymerase Inhibitors.

Figure 9A:
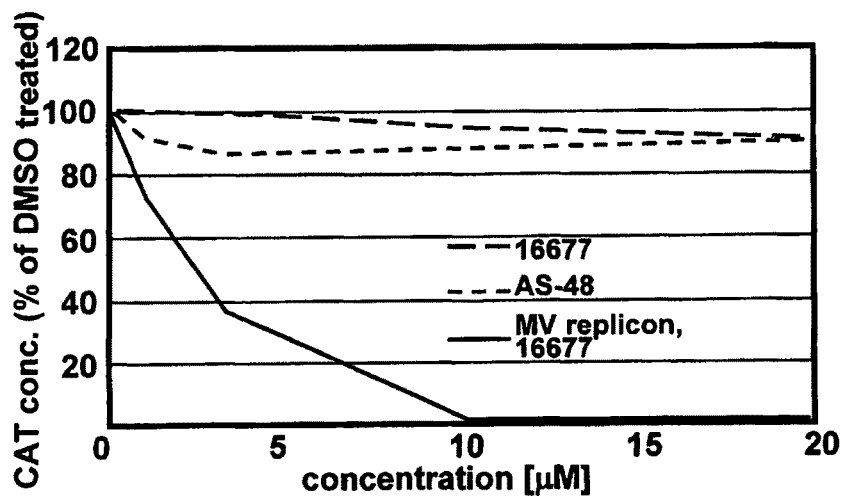
FIG. 9A illustrates that compound 16677 specifically inhibits the MV RdRp complex whereby a CAT-reporter based minireplicon assay demonstrates inhibition of the MV polymerase complex by compound 16677. BSR T7/5 cells co-transfected with the minireplicon plasmid and plasmids encoding MV nucleoprotein (N), phosphoprotein (P) and polymerase (L), all under the control of the T7 promoter, were incubated in the presence of compound 16677 or fusion inhibitor AS-48, followed by lysis and assessment of CAT concentrations. Values were determined in quadruplicate and are expressed as percent of DMSO treated controls. A comparable minireplicon system derived from Nipah virus, a related member of the paramyxovirus family, was not inhibited by compound 16677.

The initial HTS protocol did not favor the identification of inhibitors of particle assembly or release. This rendered the viral RNA-dependent RNA polymerase machinery a likely target for compound 16677. To specifically evaluate functionality of the polymerase complex, a plasmid-based sub-infection MV minireplicon reporter assay was employed (Sidhu et al., (1995) *Virology* 208(2), 800-807). This reporter construct consisted of a positive strand cDNA copy of the MV genome in which all coding and intercistronic viral sequences have been replaced by a chloramphenicol acetyl transferase (CAT) reporter gene. T7 polymerase-driven expression of this construct in the presence of MV L polymerase and polymerase cofactors N and P resulted in negative strand RNA transcripts that serve as exclusive templates for the viral polymerase complex, hence triggering MV polymerase-driven CAT expression. Consequently, the amount of CAT produced was proportional to the activity of the MV polymerase complex. When this assay was performed in the presence of different compound 16677 concentrations, the compound demonstrated a strong dose-dependent inhibition of CAT expression (FIG. 9A). This was in contrast to the essentially unchanged CAT levels found in control samples that were treated with the entry inhibitor AS-48. $IC_{50}$ concentrations of compound 16677 were notably higher in the minireplicon assay than against live virus. This likely reflects the much shorter length of the reporter gene as compared to the viral genome, providing less opportunity for interference by the compound. Importantly, the inhibitory activity of compound 16677 was specific for the MV minireplicon, since the inhibitor had no effect on a comparable minireplicon that was derived for the related Nipah virus (Halpin et al., (2004) *J Gen Virol* 85(Pt 3), 701-707). Nipah, like human parainfluenzaviruses, belongs to a different genus of the paramyxovirus family (Bossart et al., (2002) *J Virol* 76(22), 11186-11198) and shares approximately 33% protein identify with MV.

Figure 9B:
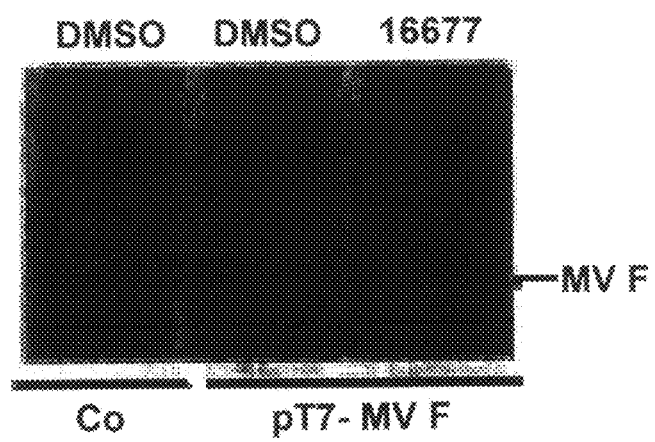
FIG. 9B illustrates that T7 polymerase is fully active in the presence of compound 16677. In vitro MV F transcription/translation in the presence of 50 µM compound 16677 or equal volumes of DMSO. Controls (Co) included DMSO and a variant of plasmid pT7-MV F that harbors the F encoding gene in reverse orientation to the T7 promoter.

Specificity of the minireplicon assay was further confirmed when an effect of compound 16677 on the cellular transcription/translation machinery or T7 polymerase function was assessed in a cell-free in vitro transcription/translation assay. A plasmid harboring the MV F gene under the control of the T7 promoter was added as template to dog reticulocyte lysates, followed by protein production in the presence or absence of compound 16677 and fractionation of samples by gel electrophoresis. Equal amounts of F protein were detected in compound-treated or untreated samples (FIG. 9B), indicating that cellular protein biosynthesis was unimpaired by the compound.

These findings are fully consistent with the low cytotoxicity observed for compound 16677 in our initial cytotoxicity assays. Taken together, they strongly argue against interference of compound 16677 with cellular factors or T7 polymerase function as alternative explanations for the reduction of reporter expression in the MV minireplicon assay. The data thus highlight compound 16677 as first-in-class compound of non-nucleoside inhibitors of the MV polymerase machinery.

Example 23

Figure 12:
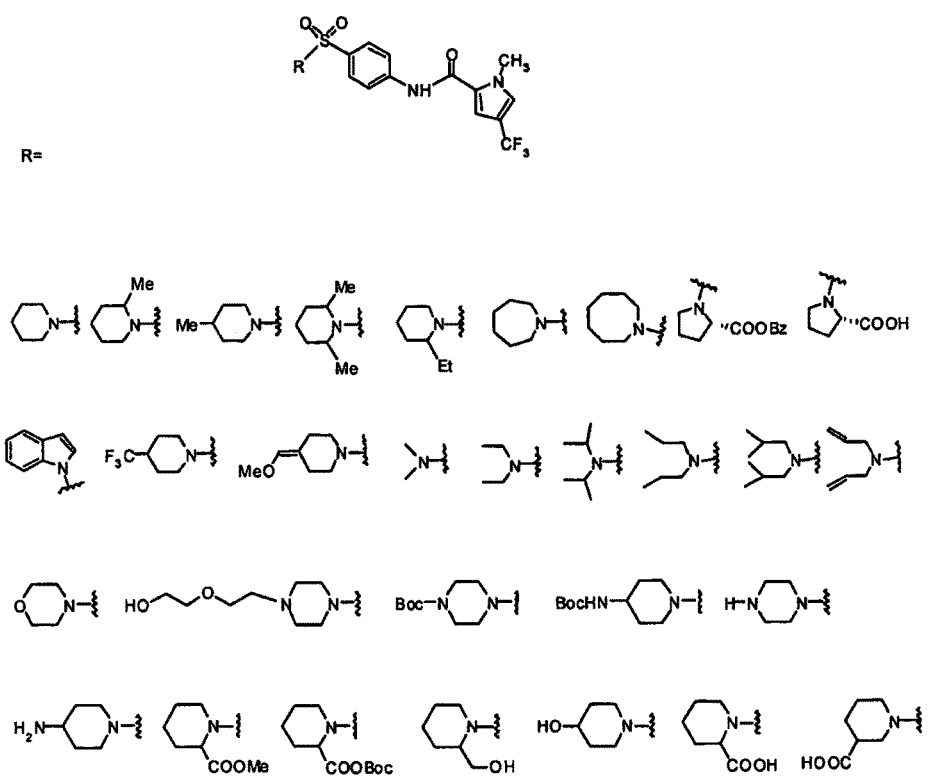
FIG. 12 illustrates the structures of embodiments of compounds of the disclosure.
Figure 13A:
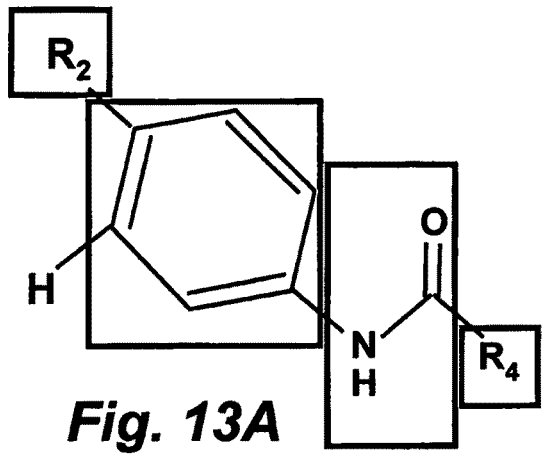
FIG. 13A illustrates the core structure of embodiments of compounds of the disclosure, wherein the four sectors subject to modification are boxed.
Figure 13B:
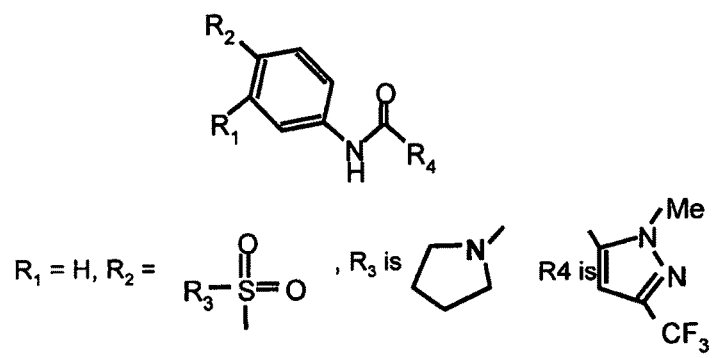
FIG. 13B illustrates structures of embodiments of compounds of the disclosure.
Figure 13C:
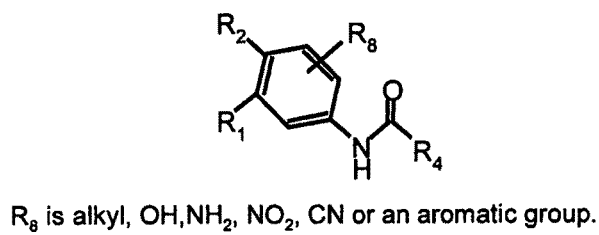
FIG. 13C illustrates structures of embodiments of compounds of the disclosure.
Figure 14:
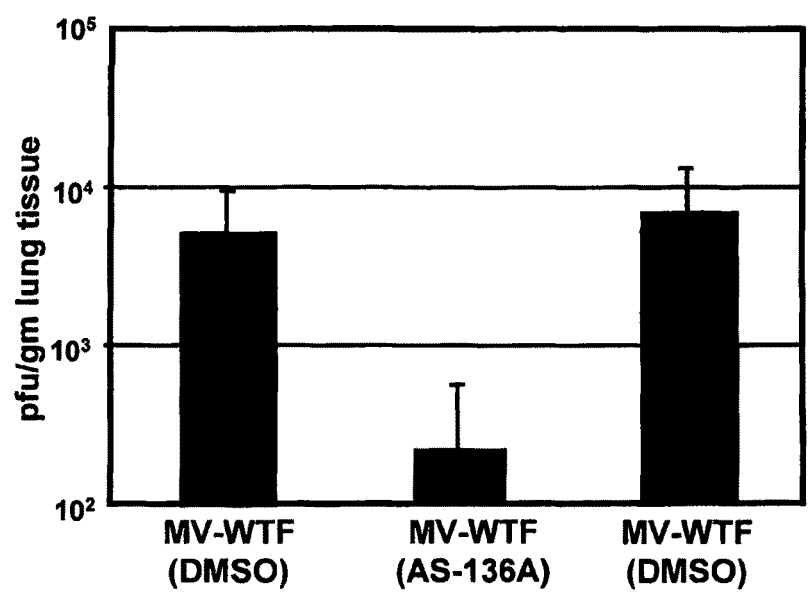
FIG. 14 illustrates the reduction in titer of measles virus in the lung tissue of reinfected rats after the administration of doses of the compound AS-136A compared to control and untreated animals.

A variety of heterocyclic rings were employed as pyrrolidine replacements while retaining the remainder of the compound 16677 structure, as shown in FIG. 12. The most active piperidine derivative, 15a, when subjected to a secondary virus titer reduction assay, revealed activity against live MV(0.012±0.017 μM, strain Alaska) and no cytotoxicity as shown in Table 1.

TABLE 1

| | | EC$_{50}$ (μM) (MV-Alaska) | | CC$_{50}$ (μM) (Vero cells) | | SI (CC$_{50}$/EC$_{50}$) | |
|---|---|---|---|---|---|---|---|
| Entry | | CPE | virus titer | MTT | Trypan blue exclusion | CPE + | Titer + |
| ID # | comp | inhibition[a] | reduction[c] | cytotoxicity[d] | assay[e] | MTT | Trypan |
| 15a | AS-136a | <2.3 | 0.014 ± 0.02 | >300 | 199 ± 27 | >130 | 14,214 |
| 15b | AS-125c | <2.3 | 0.029 ± 0.031 | >300 | 54 ± 3 | >130 | 1,862 |
| 15c | AS-127 | <2.3 | 0.035 ± 0.035 | >300 | 53 ± 4 | >130 | 1,514 |
| 15d | AS-125b | <2.3 | 0.014 ± 0.013 | >300 | 328 ± 28 | >130 | 23,429 |
| 15e | YY0169a | <2.3 | 0.087 ± 0.116 | >300 | 14 ± 2 | >130 | 160.9 |
| 15f | AS-124a | <2.3 | 0.005 ± 0.0003 | >300 | 425 ± 65 | >130 | 85,000 |
| 15g | AS-124f | <2.3 | 0.045 ± 0.034 | 16 ± 0.8 | ND | >7 | ND |
| 15h[f] | AS-85a | 14 ± 2 | ND | 100 | ND | 7.1 | ND |
| 15i[f] | AS-105 | 23 ± 10 | ND | >300 | ND | >13 | ND |
| 15j[f] | AS-103 | >13[b] | ND | 13 ± 0.7 | ND | ND | ND |
| 15k | YY0187a | 2.3 ± 0.7 | 0.02 ± 0.02 | 159 ± 12 | ND | 69.1 | ND |
| 15l | AS-625 | >75 | ND | 92 ± 9.3 | ND | <1.2 | ND |
| 15m | YY0234a | 6.3 ± 0.6 | ND | >300 | ND | >47.6 | ND |
| 15n | AS-154 | <2.3 | 0.019 ± 0.019 | >300 | 280 ± 90 | >130 | 14,737 |
| 15o | YY0213a | 3.5 ± 0.4 | 0.53 ± 0.02 | >300 | ND | >85.7 | ND |
| 15p | YY0237a | <2.3 | 0.19 ± 0.32 | >300 | ND | >130 | ND |
| 15q | YY0215a | >13.8[b] | ND | 13.8 ± 0.7 | ND | ND | ND |
| 15r | YY0247a | 3.3 ± 1.4 | ND | 34 ± 0.9 | ND | 10.3 | ND |
| 16 | AS-140 | >15[b] | ND | 15 ± 0.6 | ND | ND | ND |
| 17 | AS-155 | >75 | ND | >300 | ND | ND | ND |
| 18 | AS-627-03 | >75 | ND | 286 ± 17 | ND | <3.8 | ND |
| 19 | YY-131b | >75 | ND | 84 ± 23 | ND | <1.1 | ND |
| 20 | YY-131c | >75 | ND | >300 | ND | ND | ND |
| 23a | AS-236 | 43 ± 24 | ND | >300 | ND | >7 | ND |
| 23b | AS-270 | >75 | ND | >300 | ND | ND | ND |
| 23c | AS-254 | >75 | ND | >300 | ND | ND | ND |
| 23d | YY0168a | 14.1 ± 6.6 | ND | >300 | ND | >21.3 | ND |
| 24e | AS-244 | 28 ± 9 | ND | 126 ± 7 | ND | 4.5 | ND |
| 24f | YY0251a | >75 | ND | >300 | ND | ND | ND |
| 28a | YY-150a | 10 ± 5.6 | ND | 136 ± 3 | ND | 13.6 | ND |
| 28b | AS-248 | >38[b] | ND | 38 ± 1 | ND | ND | ND |
| 28c | AS-267 | <2.3 | 0.85 ± 0.05 | 159 ± 40 | ND | >69 | ND |
| 28d | YY0194a | 6.8 ± 0.9 | 0.57 ± 0.04 | 274 ± 19 | ND | 40.2 | ND |
| 29e | AS-251 | >75 | ND | >300 | ND | ND | ND |
| 29f | YY0173a | >75 | ND | >300 | ND | ND | ND |

[a]EC$_{50}$ not determined (ND) when CC$_{50}$ ≤ 15 μM. Values represent averages of four experiments ± SD; highest concentration assessed 75 μM, lowest concentration assessed 2.3 μM.
[b]No virus inhibition detected at CC$_{50}$ concentration.
[c]Determined only when CPE inhibition-based EC50 concentration <2.3 μM. Values represent averages of two to four experiments ± SEM; highest concentration assessed 1 μM. (ND: not determined)
[d]Values represent averages of at least three experiments ± SD; highest concentration assessed 300 μM.
[e]Determined only when virus titer reduction was assessed and MTT-assay based cytotoxicity >300 μM. (ND: not determined)

In the initial optimization of the high-throughput screening MV hit compound 16677, a preliminary SAR by structural manipulation was developed within the four principle subgroups, as shown in FIG. 13A that together make up the compound such as, but not limited to, compound 16677. A variety of modifications of the three sectors on the right either essentially abolished anti-MV activity or resulted in high cytotoxicity. However, a highly potent analog was generated by replacing the pyrrolidine ring in compound 16677 with a piperidine to give structure 15a (AS-136A) as shown in FIG. 12. The compound showed activity around 10 nM and essentially no cytotoxicity when assessed in a commercially available cytotoxicity assay. Assessment of cell proliferation activity in the presence of AS-136A using a Trypan-blue exclusion assay has yielded a CC$_{50}$ concentration of 199±27 mM, resulting in a selectivity index (CC$_{50}$/IC$_{50}$) of approximately 16,500. Previous viral entry inhibitor efforts uncovered substances effective in the 0.6-3 mM range, while one other study reported anti-MV compounds in the low micromolar range without specifying the mechanoistic basis for the inhibition Compounds 16677, AS-124A and AS-136A (15a) are novel inhibitors with potencies in the low nM range.

Example 24

To test the in vivo efficacy of the RdRp-activity blocker AS-136A, cotton rats (six animals per cohort) were infected intranasally with MV, followed by treatment of one group with 50 mg/kg body weight of the AS-136 compound twice daily for four days. The compound was delivered intraperitoneally in DMSO and the first injection administered one hour before infection. Control animals were treated with DMSO only. All animals were euthanized on day 4.

Virus titration from lung homogenates demonstrated a strong reduction in viral titers in the presence of the compound. As shown in FIG. 14, for example, control animals had an average of $10^{3.6±0.3}$ TCID$_{50}$ of virus/gm of lung tissue, whereas in four out of six treated animals virus load was below the level of detection (<$10^1$ TCID$_{50}$ of virus/gm lung tissue). In two animals, viral titers averaged $10^{2.8±0.2}$TCID$_{50}$ of virus/gm lung tissue. Three control animals, which had not been treated with either compound or DMSO, had viral titers of $10^{3.7\pm0.4}$ TCID$_{50}$ of virus/gm lung tissue. Histological analysis of lung tissue still demonstrated a low grade interstitial pneumonia in treated and control animals. These results indicated that compound AS-136A has antiviral activity against measles virus in vivo.

We claim:

1. A therapeutic composition comprising a pharmaceutically acceptable carrier and a compound of the following formula:

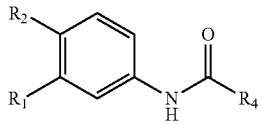

or salts thereof wherein, if $R_1$=H, $R_2$=—SO$_2$R$_3$, and if $R_2$=H, $R_1$=—SO$_2$R$_3$, and wherein $R_3$ is

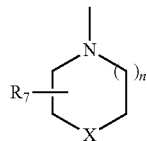

wherein, X of $R_3$ is CH$_2$, CHOH, CHCH$_3$, CHCF$_3$, CHNHBoc, CHNH$_2$, O, NH, NBoc, NMe, or NCH$_2$CH$_2$OCH$_2$CH$_2$OH;
n is 0-3;
$R_7$ is H, Me, Et, CH$_2$OH, COOH, COOMe, or COOBz; and, wherein $R_4$ is:

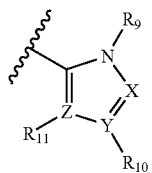

wherein, X of $R_4$ is N or CH;
Y is N or C, if Y is N then $R_{10}$ is absent;
Z is N or C, if Y is N then $R_{11}$ is absent;
$R_9$ is H, alkyl, CH$_2$OH, or CH$_2$NH$_2$;
$R_{10}$ is H, CH$_3$, CF$_3$, Cl, Br, F, CHF$_2$, CH$_2$F, or CH$_2$OH; and
$R_{11}$ is selected from: H, alkyl, F, Cl, or Br.

2. The therapeutic composition of claim 1, wherein $R_1$ is H and $R_2$ is —SO$_2$R$_3$.

3. The therapeutic composition of claim 1, wherein $R_4$ is

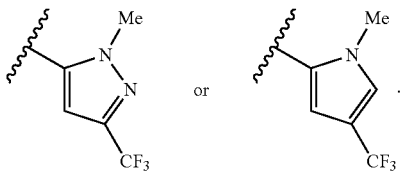 [SMILES: *c1cc(C(F)(F)F)nn1C ; *c1cc(C(F)(F)F)cn1C]

4. The therapeutic composition of claim 1, wherein the compound is selected from;
   1-methyl-3-(trifluoromethyl)-N-[4-(pyrrolidinylsulfonyl)phenyl]-1H-pyrazole-5-carboxamide;
   1-methyl-3-(trifluoromethyl)-N-[4-(piperidin-1-ylsulfonyl)phenyl]-1H-pyrazole-5-carboxamide; and
   1-methyl-3-(trifluoromethyl)-N-(4-(azepan-1-ylsulfonyl)phenyl)-1H-pyrazole-5-carboxamide or salts thereof.

5. The therapeutic composition of claim 1, wherein the pharmaceutically acceptable carrier is selected from a sugar, lactose, glucose, sucrose, starch, corn starch, potato starch, cellulose, sodium carboxymethyl cellulose, ethyl cellulose, cellulose acetate, sorbitol, mannitol, alginic acid, tragacanth, malt, gelatin, and agar.

6. The therapeutic composition of claim 1, wherein the pharmaceutically acceptable carrier is selected from cocoa butter, suppository waxes, peanut oil, cottonseed oil, safflower oil, sesame oil, olive oil, corn oil, soybean oil, glycols, propylene glycol, glycerin, ethyl oleate, and ethyl laurate.

7. The therapeutic composition of claim 1, wherein the pharmaceutically acceptable carrier is selected from talc, calcium carbonate, calcium phosphate, magnesium hydroxide, and aluminum hydroxide.

8. The therapeutic composition of claim 1, wherein the pharmaceutically acceptable carrier is selected from isotonic saline, ringer's solution, ethyl alcohol, and phosphate buffer.

9. A composition comprising a compound 1-methyl-3-(trifluoromethyl)-N-[4-(piperidin-1-ylsulfonyl)phenyl]-1H-pyrazole-5-carboxamide, derivative, or salt thereof.

10. A pharmaceutically acceptable salt of 1-methyl-3-(trifluoromethyl)-N-[4-(pyrrolidinylsulfonyl)phenyl]-1H-pyrazole-5-carboxamide or derivative thereof.

* * * * *

UNITED STATES PATENT AND TRADEMARK OFFICE
CERTIFICATE OF CORRECTION

PATENT NO.        : 8,729,059 B2
APPLICATION NO.   : 12/526373
DATED             : May 20, 2014
INVENTOR(S)       : Plemper et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1191 days.

Signed and Sealed this
Eleventh Day of August, 2015

Michelle K. Lee
*Director of the United States Patent and Trademark Office*